US008257706B2

(12) United States Patent
McDonagh et al.

(10) Patent No.: US 8,257,706 B2
(45) Date of Patent: Sep. 4, 2012

(54) CD30 BINDING AGENTS AND USES THEREOF

(75) Inventors: Charlotte McDonagh, Winchester, MA (US); Paul Carter, Mercer Island, WA (US)

(73) Assignee: Seattle Genetics, Inc., Bothell, WA (US)

( * ) Notice: Subject to any disclaimer, the term of this patent is extended or adjusted under 35 U.S.C. 154(b) by 299 days.

(21) Appl. No.: 12/438,604

(22) PCT Filed: Aug. 24, 2007

(86) PCT No.: PCT/US2007/076830
§ 371 (c)(1),
(2), (4) Date: May 20, 2009

(87) PCT Pub. No.: WO2008/025020
PCT Pub. Date: Feb. 28, 2008

(65) Prior Publication Data
US 2010/0239571 A1  Sep. 23, 2010

Related U.S. Application Data

(60) Provisional application No. 60/840,161, filed on Aug. 25, 2006.

(51) Int. Cl.
*A61K 39/395* (2006.01)
*C07K 16/18* (2006.01)
(52) U.S. Cl. ............... 424/133.1; 530/387.1; 530/387.3; 530/388.1
(58) Field of Classification Search ............... 424/133.1; 530/387.1, 387.3, 388.1
See application file for complete search history.

(56) References Cited

U.S. PATENT DOCUMENTS

| 6,033,876 | A | 3/2000 | Lemke et al. | |
|---|---|---|---|---|
| 7,090,843 | B1 | 8/2006 | Francisco et al. | |
| 7,387,776 | B2 | 6/2008 | Keler et al. | |
| 2006/0008883 | A1* | 1/2006 | Lazar et al. | 435/69.7 |
| 2007/0148171 | A1 | 6/2007 | Lazar et al. | |
| 2008/0213289 | A1 | 9/2008 | Francisco et al. | |
| 2008/0317747 | A1 | 12/2008 | Francisco et al. | |
| 2009/0148942 | A1* | 6/2009 | McDonagh et al. | 435/375 |

FOREIGN PATENT DOCUMENTS

| WO | WO0243661 A2 | 6/2002 |
|---|---|---|
| WO | WO03043583 A2 | 5/2003 |
| WO | WO2005001038 A2 | 1/2005 |

OTHER PUBLICATIONS

ATCC search output ("PTA-6951" and "hAC10 2-6D5"; pp. 1-2; May 3, 2011).*
Al-Lazikani et al., "Standard Conformations for the Canonical Structures of Immunoglobulins," J. Mol. Biol., 1997, 273, 927-948.
Blum et al., "Serious Pulmonary Toxicity with SGN-30 and Gemcitabine, Vinorelbine, and Liposomal Doxorubicin in Patients with Relapsed/Refractory Hodgkin Lymphoma (HL): Cancer and Leukemia Group B (CALGB) 50502," Abstract No. 232, 2008 ASH Annual Meeting Abstracts, 2008, 112, 92.
Borchmann et al., "The human anti-CD30 antibody 5F11 shows in vitro and in vivo activity against malignant lymphoma," Blood, 2003, 102, 3737-3742.
Bowen et al., "Functional Effects of CD30 on a Large Granular Lymphoma Cell Line, YT," J. Immunol., 1993, 151, 5896-5906.
Chothia et al., "Domain Association in Immunoglobulin Molecules the Packing of Variable Domains," J. Mol. Biol., 1985, 186, 651-663.
Chothia et al., "Canonical Structures for the Hypervariable Regions of Immunoglobulins," J. Mol. Biol., 1987, 196, 901-917.
Chothia et al., "Conformations of immunoglobulin hypervariable regions," Nature, 1989, 342, 877-883.
Francisco et al., "cAC10-vcMMAE, an anti-CD30-monomethyl auristatin E conjugate with potent and selective antitumor activity," Blood, 2003, 102, 1458-65.
Hammond et al., "A Humanized Anti-CD30 Monoclonal Antibody, XmAbTM 2513, with Enhanced in Vitro Potency Against CD30-Positive Lymphomas Mediated by High Affinity Fc-Receptor Binding," poster presentation at the American Society of Hematology 47th Annual Meeting and Exposition, Dec. 10-13, 2005, Atlanta, GA.
Iwahashi et al., "CDR substitutions of a humanized monoclonal antibody (CC49): contributions of individual CDRs to antigen binding and immunogenicity," Molecular Immunology, 1999, 36, 1079-1091.
Padlan et al., "Identification of specificity-determining residues in antibodies," FASEB, 1995, 9, 133-139.
Schlapschy et al., "Functional humanization of an anti-CD30 Fab fragment for the immunotherapy of Hodgkin's lymphoma using an in vitro evolution approach," Protein Eng. Des. Sel., 2004, 17, 847-860.
Tamura et al., "Structural Correlates of an Anticarcinoma Antibody: Identification of Specificity-Determining Residues (SDRs) and Development of a Minimally Immunogenic Antibody Variant by Retention of SDRs Only," the Journal of Immunology, 2000, 164, 1432-1441.
Tomlinson et al., "The structural repertoire of the human Vκ domain," the EMBO Journal, 1995, 14, 4628-4638.

* cited by examiner

*Primary Examiner* — Lynn Bristol
(74) *Attorney, Agent, or Firm* — Seattle Genetics, Inc.

(57) ABSTRACT

This invention relates to CD30 binding agents and methods of using such binding agents for treating disease characterized by expression of CD30 antigen.

22 Claims, 2 Drawing Sheets

CD30 BINDING AGENTS AND USES THEREOF

This application is the national stage filing under 35 U.S.C. §371 of International Application No. PCT/PCT/US2007/076830 filed Aug. 24, 2007 and published Feb. 28, 2008 as International Publication No. WO 2008/025020 which in turn claims the benefit of U.S. Provisional Application No. 60/840,161, filed Aug. 25, 2006, the disclosure of which is incorporated by reference herein.

REFERENCE TO A SEQUENCE LISTING

This application includes a sequence listing as a text file named, "0030-00411US ST25.txt created Feb. 19, 2009 and containing 79,380 bytes. The material contained in this text file is incorporated by reference in its entirety for all purposes.

BACKGROUND

The CD30 cell surface molecule is a member of the tumor necrosis factor receptor (TNF-R) superfamily. This family of molecules has variable homology among its members and includes nerve growth factor receptor (NGFR), CD120(a), CD120(b), CD27, CD40 and CD95. These molecules are typically characterized by the presence of multiple cysteine-rich repeats in the extracytoplasmic region (see, e.g., de Bruin et al., 1995, *Leukemia* 9:1620-1627). Members of this family are believed to be involved in the regulation of the proliferation and differentiation of lymphocytes.

CD30 is a type I transmembrane glycoprotein with six (human) or three (murine and rat) cysteine-rich repeats with a central hinge sequence. CD30 exists as a 120 kDa membrane molecule. It is shed from the cell surface as a soluble protein (sCD30) of approximately 90 kDa. Shedding of sCD30 occurs as an active process of viable CD30 cells. cDNAs encoding the CD30 protein have been cloned from expression libraries using monoclonal antibodies Ki-1 and Ber-H2 (see, e.g., Schwab et al., 1982, *Nature* 299:65). The mouse and rat CD30 cDNAs have been found to encode 498 and 493 amino acids, respectively. Human CD30 cDNA encodes an additional 90 amino acids, partially duplicated from one of the cysteine rich domains. The CD30 gene has been mapped to 1p36 in humans and 5q36.2 in rats.

CD30 is preferentially expressed by activated lymphoid cells. Stimulation of CD30 in lymphoid cells has been shown to induce pleiotropic biological effects, including proliferation, activation, differentiation and cell death, depending on cell type, stage of differentiation and presence of other stimuli (see, e.g., Grass et al., 1994, *Blood* 83:2045-2056).

CD30 is expressed on a subset of non-Hodgkin's lymphomas (NHL), including Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and centroblastic/centrocytic (cb/cc) follicular lymphomas (Stein et al., 1985, *Blood* 66:848; Miettinen, 1992, *Arch. Pathol. Lab. Med.* 116:1197; Pins et al., 1990, *Histopathology* 17:211; Burns et al., 1990, *Am. J. Clin. Pathol.* 93:327; and Eckert et al., 1989, *Am. J. Dermatopathol.* 11:345). CD30 expression has also been reported on several virally-transformed lines such as human T-Cell Lymphotrophic Virus I or II transformed T-cells, and Epstein-Barr Virus transformed B-cells (Stein et al, 1985, *Blood* 66:848; Andreesen et al, 1984, *Blood* 63:1299). CD30 expression has been documented in embryonal carcinomas, nonembryonal carcinomas, malignant melanomas, mesenchymal tumors, and myeloid cell lines and macrophages at late stages of differentiation (Schwarting et al., 1989, *Blood* 74:1678; Pallesen et al, 1988, *Am J. Pathol.* 133:446; Mechtersheimer et al, 1990, *Cancer* 66:1732; Andreesen et al., 1989, *Am. J. Pathol.* 134:187).

CD30 expression also has been reported to increased or altered in a variety of autoimmune and inflammatory diseases, including atopic allergy (atopic dermatitis, atopic asthma, rhinoconjunctivitis, allergic rhinitis), systemic lupus erythematosus, systemic sclerosis (scleroderma), graft versus host disease (GVHD), HIV and EBV infection, measles, Omenn's syndrome, ulcerative colitis, rheumatoid arthritis, multiple sclerosis, psoriasis, Hashimoto's thyroiditis, primary biliary cirrhosis, Sjogren's syndrome, Wegener's granulomatosis, and tuberculosis (Gruss et al., 1997, Immunol. Today 18:156-163; Hone and Watababe, 1998, Sem. Immunol. 10:457-470; Bengtsson, 2001, *Allergy* 56:593-603; Gerli et al., 2001, *Trends Immunol.* 22:72-77).

Murine anti-CD30 mAbs have been generated by immunization of mice with HD cell lines or purified CD30 antigen. Such antibodies include AC10, originally termed C10 (Bowen et al, 1993. *J. Immunol.* 151:5896-5906), HeFi-1 (Hecht et al, 1985, *J. Immunol.* 134:4231-4236); and BerH2 (Schwarting et al., 1989, *Blood* 74:1678-1689). However, murine antibodies do not constitute ideal therapeutic agents for humans.

There remains a need, therefore, for additional therapeutic agents directed to CD30. More specifically, there exists a need for humanized antibodies specific to CD30, because of their potential as therapeutic agents in the treatment of diseases associated with CD30 expressing cells.

SUMMARY

The present invention provides CD30 binding agents and methods of using such binding agents. The binding agents comprise the amino acid sequence(s) of a humanized heavy chain variable region and/or a humanized light chain variable region, or a derivative(s) thereof, and specifically bind to the extracellular domain of CD30.

In some embodiments, the binding agents can be antibodies and antigen-binding fragments thereof that specifically bind to human CD30. The antibodies and antigen-binding fragments can include an immunoglobulin heavy chain variable region and/or an immunoglobulin light chain variable region, or a derivative(s) thereof, that binds to the extracellular domain of CD30. Also included are kits and pharmaceutical compositions comprising such CD30 binding agents In some embodiments, the antibody includes the amino acid sequence of a humanized heavy chain variable region in which the framework region (FR) has an amino acid sequence at least 90% identical to the amino acid sequence of the human germline $V_H1-2$ or $V_H1-18$. In some embodiments, the antibody includes a light chain variable region in which the FR has an amino acid sequence at least 90% identical to the amino acid sequence of the human germline $V_\kappa$ exon B3. In some embodiments, the antibody includes a heavy chain variable region in which the framework region (FR) has an amino acid sequence at least 90% identical to the amino acid sequence of the human germline $V_H1-2$ or $V_H1-18$, and a light chain variable region in which the FR has an amino acid sequence at least 90% identical to the amino acid sequence of the human germline $V_\kappa$ exon B3.

In some embodiments, the heavy chain framework region includes an amino acid substitution at position 71, at position 91, or at positions 71 and 91, according to the numbering system of Kabat et al. In some embodiments, the amino acid at position 71 is valine. In some embodiments, the amino acid at position 91 is phenylalanine.

In some embodiments, the light chain framework region has an amino acid substitution at position 25, position 33, or positions 25 and 33, according to the numbering system of Kabat et al. In some embodiments, the amino acid at position 25 is alanine. In some embodiments, the amino acid at position 33 is methionine.

In some embodiments, the CDRs of the CD30 binding antibody include the heavy chain and light chain variable region CDR1, CDR2, and CDR3 of the antibody AC10. In some embodiments, each CDR can have zero, one or two conservative amino acid substitution with respect to a CDR of antibody AC10.

In some embodiments, the heavy chain variable region includes the amino acid sequence of SEQ ID NO:4, SEQ ID NO:9, SEQ ID NO:14 or SEQ ID NO:19. In some embodiments, the light chain variable region includes the amino acid sequence of SEQ ID NO: 26, SEQ ID NO:31, SEQ ID NO:36, or SEQ ID NO:41.

In some embodiments, the antibody includes a human IgG constant region. In some embodiments, the isotype of the IgG constant region is $IgG_1$, $IgG_2$, $IgG_3$, or $IgG_4$. In some embodiments, the antibody has a heavy chain in which the amino acid sequence is of SEQ ID NO:7, SEQ ID NO:12, SEQ ID NO:17 or SEQ ID NO:22. In some embodiments, the antibody includes a human light chain constant domain, e.g., a kappa constant domain. In some embodiments, the antibody has a light chain in which the amino acid sequence is of SEQ ID NO:29, SEQ ID NO:34, SEQ ID NO:39, or SEQ ID NO:44.

In some embodiments, the antibody includes an antibody heavy chain variable domain and light chain variable domain with the amino acid sequences of SEQ ID NO:4 and SEQ ID NO:26, respectively; SEQ ID NO:4 and SEQ ID NO:31, respectively; SEQ ID NO:4 and SEQ ID NO:36, respectively; SEQ ID NO:4 and SEQ ID NO:41, respectively; SEQ ID NO:9 and SEQ ID NO:26, respectively; SEQ ID NO:14 and SEQ ID NO:26, respectively; SEQ ID NO:19 and SEQ ID NO:26, respectively; or SEQ ID NO:19 and SEQ ID NO:41, respectively.

In some embodiments, the antibody includes a heavy chain and a light chain in which the heavy chain has the amino acid sequence of SEQ ID NO:7, SEQ ID NO:12, SEQ ID NO:17 or SEQ ID NO:22; and the light chain has the amino acid sequence of SEQ ID NO:29, SEQ ID NO:34, SEQ ID NO:39 or SEQ ID NO:44. In some embodiments, the antibody includes a heavy chain and a light chain with the amino acid sequences of SEQ ID NO:7 and SEQ ID NO:29, respectively; SEQ ID NO:7 and SEQ ID NO:34, respectively: SEQ ID NO:7 and SEQ ID NO:39, respectively; SEQ ID NO:7 and SEQ ID NO:44, respectively; SEQ ID NO:12 and SEQ ID NO:29, respectively; SEQ ID NO:17 and SEQ ID NO:29, respectively; SEQ ID NO:22 and SEQ ID NO:29, respectively; or SEQ ID NO:22 and SEQ ID NO:44, respectively.

In some embodiments, the antibody is an antigen-binding antibody fragment that specifically binds to human CD30. The antibody fragment can be, for example, a Fab, Fab', $F(ab')_2$, Fv fragment, a diabody, a linear antibody, an scFv, or an scFv-Fc.

In some embodiments, the CD30 binding agent competes for binding to CD30 with antibody AC10. In some embodiments, the CD30 binding agent exhibits a cytotoxic or cytostatic effect in the absence of effector cells or in the absence of conjugation to a therapeutic agent. In some embodiments, the CD30 binding agent includes a constant region or portion thereof which mediates an effector function, including e.g., ADCC, CDC or ADCP. In some embodiments, the CD30 binding agent is conjugated to a cytotoxic, cytostatic or immunomodulatory agent. The cytotoxic agent can include, e.g., auristatin E, MMAE and MMAF. In some embodiments, the antibody has a detectable label.

In some embodiments, the CD30 binding agent is an antibody produced by a cell line having ATCC Accession No. PTA-6951. In some embodiments, the antibody is a humanized monoclonal antibody that competes for binding to CD30 (e.g., human CD30) with the antibody produced the cell line having ATCC Accession No. PTA-6951.

In another aspect, polynucleotides are provided that encode CD30 binding agents that specifically bind to human CD30. In some embodiments, a polynucleotide includes the sequence of SEQ ID NO:3, SEQ ID NO:8, SEQ ID NO:13, SEQ ID NO:18, SEQ ID NO:25, SEQ ID NO:30, SEQ ID NO:35, or SEQ ID NO:40. In some embodiments, a polynucleotide encodes a heavy chain variable domain and/or a light chain variable domain, e.g., the nucleotide sequences of SEQ ID NO:3 and SEQ ID NO:25, respectively; SEQ ID NO:3 and SEQ ID NO:30, respectively; SEQ ID NO:3 and SEQ ID NO:35, respectively; SEQ ID NO:3 and SEQ ID NO:40, respectively; SEQ ID NO:8 and SEQ ID NO:25, respectively; SEQ ID NO:13 and SEQ ID NO:25, respectively; SEQ ID NO:18 and SEQ ID NO:25, respectively; or SEQ ID NO:18 and SEQ ID NO:40, respectively.

In some embodiments, a polynucleotide encodes a heavy chain and/or a light chain which includes the nucleotide sequences of SEQ ID NO:5 and SEQ ID NO:27, respectively; SEQ ID NO:5 and SEQ ID NO:32, respectively; SEQ ID NO:5 and SEQ ID NO:37, respectively; SEQ ID NO:5 and SEQ ID NO:42, respectively; SEQ ID NO:10 and SEQ ID NO:27, respectively; SEQ ID NO:15 and SEQ ID NO:27, respectively; SEQ ID NO:20 and SEQ ID NO:27, respectively; or SEQ ID NO:20 and SEQ ID NO:42, respectively.

In another aspect, methods are provided for inhibiting the proliferation or differentiation of tumor cells expressing CD30. Such methods can include administering to the cells an effective amount of a CD30 binding agent (e.g., an antibody or antigen-binding fragment thereof) that specifically binds to and inhibits the proliferation or differentiation of cells expressing human CD30. In some embodiments, the tumor cells are B lymphoblastoid cells.

In another aspect, methods are provided for inducing the depletion of peripheral B cells which are associated with an immune disorder. Such methods can include administering a CD30 binding agent (e.g., an antibody or antigen-binding fragment thereof) that specifically binds to human CD30. In some embodiments, the immune disorder can be rheumatoid arthritis, systemic lupus erythematosus, multiple sclerosis or inflammatory bowel disease).

In another aspect, pharmaceutical compositions are provided in which the composition includes a CD30 binding agent (e.g., an antibody or antigen-binding fragment thereof) that specifically binds to human CD30 and a pharmaceutically acceptable excipient. In some embodiments, the binding agent is an antibody, such as the antibody produced by the cell line having ATCC Accession No. PTA-6951. In some embodiments, the CD30 binding agent is conjugated to a cytotoxic, cytostatic or therapeutic agent. In some embodiments, the pharmaceutical composition is used in a method for treating an immune disorder, an infectious disease, or cancer.

The present invention may be more fully understood by reference to the following detailed description, non-limiting examples of specific embodiments, and the appended figures and sequence listing.

DETAILED DESCRIPTION

Figure 1:
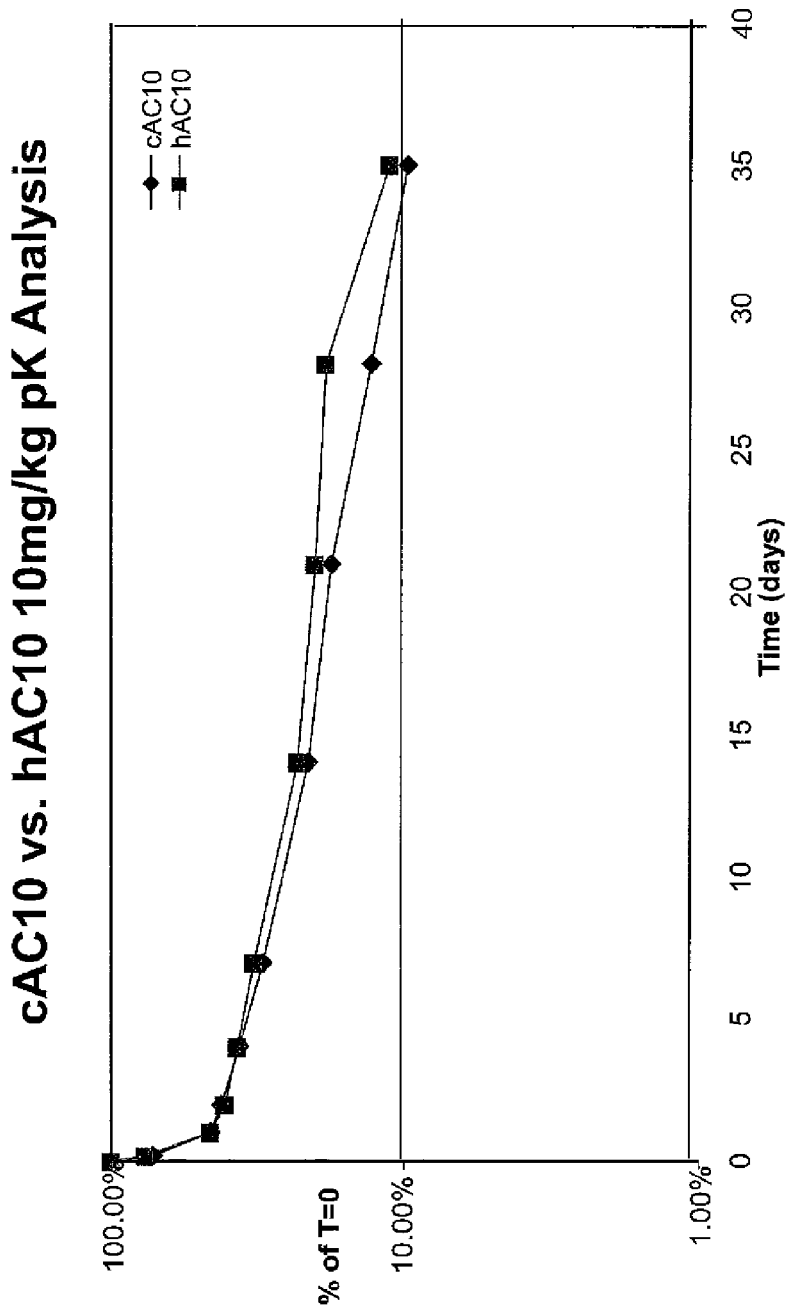
FIG. 1 illustrates the pharmacokinetic profiles of cAC10 (chimeric AC10) antibody and a hAC10 (humanized AC10) antibody.

The present invention provides CD30 binding agents and methods for using such binding agents for the treatment of CD30-expressing cancers and immunological disorders. The CD30 binding agents include at least one polypeptide that comprises an antibody heavy chain variable region and/or an antibody light chain variable region, or a derivative thereof. In some embodiments, the CD30 binding agents compete with the murine monoclonal antibody (mAb) AC10 or a human-murine chimeric AC10 (cAC10) for binding to human CD30.

In some aspects, the CD30 binding agent has a cytotoxic, cytostatic and/or immunomodulatory effect on CD30-expressing cells. Such an effect can be mediated, for example, by the depletion or inhibition of the proliferation or differentiation of CD30-expressing cells. In some embodiments, the CD30 binding agent can mediate effector function. In some embodiments, the CD30 binding agent is conjugated to a therapeutic agent. In some embodiments, depletion or inhibition of CD30-expressing cells is mediated independently of effector function (e.g., without recruiting or activating cytotoxic white blood cells, e.g., natural killer (NK) cells, phagocytic cells (e.g., macrophages), or serum complement components) or without conjugation to a therapeutic agent.

In some aspects, the compositions and methods relate to antibodies and antibody derivatives that bind to CD30. The anti-CD30 antibodies and derivatives include the amino acid sequence of a humanized heavy chain variable region and/or a humanized light chain variable region, or a derivative thereof. In some embodiments, the anti-CD30 antibodies or derivatives include at least one immunoglobulin constant region domain, or an entire constant region of an antibody, such as a human constant region or a functionally active portion thereof. In some embodiments, the antibody constant region or domain(s) is of the IgG class. In other embodiments, the anti-CD30 antibodies comprise an antibody fragment.

For clarity of disclosure, and not by way of limitation, the detailed description of the invention is divided into the subsections which follow.

I. Definitions and Abbreviations

When a trade name is used herein, reference to the trade name also refers to the product formulation, the generic drug, and the active pharmaceutical ingredient(s) of the trade name product, unless otherwise indicated by context.

The terms "CD30 binding agent" and "anti-CD30 binding agent" as used herein refers to a molecule that specifically binds to CD30, such as an anti-CD30 antibody, a derivative or a fragment of an anti-CD30 antibody, or other agent that includes an antibody heavy and/or light chain variable region.

As used herein, the term "functional," in the context of a CD30 binding agent, indicates that the binding agent is capable of specifically binding to CD30.

The terms "inhibit" or "inhibition of" as used herein means to reduce by a measurable amount, or to prevent entirely.

The term "deplete," in the context of the effect of a CD30 binding agent on CD30-expressing cells, refers to a reduction in the number of or elimination of the CD30-expressing cells.

"Native antibodies" and "native immunoglobulins" are defined herein as heterotetrameric glycoproteins, typically of about 150,000 daltons, composed of two light (L) chain and two heavy (H) chains. Each light chain is covalently linked to a heavy chain by a disulfide bond to form a heterodimer. The heterotetramer is formed by covalent disulfide linkage between the two heavy chains of such heterodimers. Although the light and heavy chains are linked together by a disulfide bond, the number of disulfide linkages between the two heavy chains varies by immunoglobulin (Ig) isotype. Each heavy and light chain also has regularly spaced intrachain disulfide bridges. Each heavy chain has at the amino-terminus a variable domain ($V_H$), followed by three or four constant domains ($C_H1$, $C_H2$, $C_H3$, and/or $C_H4$, as appropriate for the antibody type), as well as a hinge (J) region between $C_H1$ and $C_H2$. Each light chain has two domains, an amino-terminal variable domain ($V_L$) and a carboxy-terminal constant domain ($C_L$). The $V_L$ domain associates non-covalently with the $V_H$ domain, whereas the $C_L$ domain is commonly covalently linked to the $C_H1$ domain via a disulfide bond. Particular amino acid residues are believed to form an interface between the light and heavy chain variable domains (see, e.g., Chothia et al., 1985, *J. Mol. Biol.* 186:651-663).

The term "hypervariable" refers to certain sequences within the variable domains of an immunoglobulin that differ extensively in sequence among antibodies and contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). The locations of the CDRs are defined by sequence comparison in Kabat et al., 1991, In: *Sequences of Proteins of Immunological Interest,* 5th Ed. Public Health Service, National Institutes of Health, Bethesda, Md., whereas HVLs are structurally defined according to the three-dimensional structure of the variable domain, as described by Chothia and Lesk, 1987, *J. Mol. Biol.* 196:901-917. As defined by Kabat, CDR-L1 is positioned at about residues 24-34, CDR-L2 at about residues 50-56, and CDR-L3 at about residues 89-97 in the light chain variable domain. CDR-H1 is positioned at about residues 31-35, CDR-H2 at about residues 50-65, and CDR-H3 at about 95-102 in the heavy chain variable domain.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains to close proximity to each other as well as to the CDRs from the other chain. The resulting conformation contributes to the antigen binding site (see, e.g., Kabat et al., 1991, NIH Publ. No. 91-3242, Vol. I, pages 647-669), although not all CDR residues are necessarily directly involved in antigen binding.

FR residues and Ig constant domains are typically not directly involved in antigen binding, but may contribute to antigen binding or mediate antibody effector function. Some FR residues can have a significant effect on antigen binding in at least three ways: by noncovalently binding directly to an epitope, by interacting with one or more CDR residues, and by affecting the interface between the heavy and light chains. The constant domains may mediate various Ig effector functions, such as participation of the antibody in antibody dependent cellular cytotoxicity (ADCC), complement dependent cytotoxicity (CDC) and/or antibody dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, and $IgG_4$; and $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

The terms "antibody", "anti-CD30 antibody", "humanized anti-CD30 antibody", and "variant humanized anti-CD30 antibody" are used herein in the broadest sense and specifically encompass full-length and native antibodies, monoclonal antibodies (including full-length monoclonal antibodies), polyclonal antibodies, multispecific antibodies (e.g., bispecific antibodies), and antibody fragments thereof, such as variable domains and other portions of antibodies that exhibit a desired biological activity (e.g., CD30 binding).

The terms "monoclonal antibody" or "mAb" refer to an antibody obtained from a population of substantially homogeneous antibodies; that is, the individual antibodies comprising the population are identical except for naturally occurring mutations that may be present in minor amounts. Monoclonal antibodies are highly specific, being directed against a single antigenic determinant, also referred to as an epitope. The modifier "monoclonal" is indicative of a substantially homogeneous population of antibodies directed to the identical epitope and is not to be construed as requiring production of the antibody by any particular method. Monoclonal antibodies can be made by any technique or methodology known in the art; for example, the hybridoma method first described by Köhler et al., 1975, *Nature* 256:495, or recombinant DNA methods known in the art (see, e.g., U.S. Pat. No. 4,816,567). In another example, monoclonal antibodies also can be isolated from phage antibody libraries, using techniques described in Clackson et al., 1991, *Nature* 352: 624-628, and Marks et al., 1991, *J. Mol. Biol.* 222: 581-97.

The term "chimeric" antibody, as used herein, refers to a type of monoclonal antibody in which a portion of or the complete amino acid sequence in one or more regions or domains of the heavy and/or light chain is identical with, homologous to, or a variant of, the corresponding sequence in a monoclonal antibody from another species or belonging to another immunoglobulin class or isotype, or from a consensus sequence. An example of a chimeric antibody is one which has a variable region derived from a non-human monoclonal antibody and a human IgG immunoglobulin constant region. Chimeric antibodies include fragments of such antibodies, provided that the antibody fragment exhibits the desired biological activity of its parent antibody, for example binding to the same epitope (see, e.g., U.S. Pat. No. 4,816, 567; and Morrison et al., 1984, *Proc. Natl. Acad. Sci. USA* 81:6851-6855). Methods for producing chimeric antibodies are known in the art. (See, e.g., Morrison, 1985, *Science* 229:1202; Oi et al., 1986, *BioTechniques* 4:214; Gillies et al., 1989, *J. Immunol. Methods* 125:191-202; U.S. Pat. Nos. 5,807,715; 4,816,567; and 4,816,397.)

The terms "antibody fragment", "anti-CD30 antibody fragment", "humanized anti-CD30 antibody fragment", and "variant humanized anti-CD30 antibody fragment" refer to a portion of a full-length anti-CD30 antibody in which a variable region or a functional capability is retained, for example, specific CD30 epitope binding. Examples of antibody fragments include, but are not limited to, a Fab, Fab', $F(ab')_2$, Fd, Fv, scFv and scFv-Fc fragment, a diabody, a linear antibody, a minibody and a multispecific antibody formed from antigen-binding antibody fragments.

A "single-chain Fv" or "scFv" antibody fragment is a single chain Fv variant comprising the $V_H$ and $V_L$ domains of an antibody in which the domains are present in a single polypeptide chain and which is capable of recognizing and binding antigen. The scFv polypeptide optionally contains a polypeptide linker positioned between the $V_H$ and $V_L$, domains that enables the scFv to form a desired three-dimensional structure for antigen binding, (see, e.g., Plückthun, 1994, In *The Pharmacology of Monoclonal Antibodies*, Vol. 113, Rosenburg and Moore eds., Springer-Verlag, New York, pp. 269-315).

The term "diabody" refers to a small antibody fragment having two antigen-binding sites. Each fragment contains a heavy chain variable domain ($V_H$) concatenated to a light chain variable domain ($V_L$) to form a $V_H$-$V_L$, or $V_L$-$V_H$ polypeptide. By using a linker that is too short to allow pairing between the two domains on the same chain, the linked $V_H$-$V_L$ domains are forced to pair with complementary domains of another chain, creating two antigen-binding sites. Diabodies are described more fully, for example, in EP 0 404 097; WO 93/11161; and Hollinger et al., 1993, *Proc. Natl. Acad. Sci. USA* 90:6444-6448.

The term "linear antibody" refers to an antibody that has a pair of tandem Fd segments ($V_H$-$C_H$1-$V_H$-$C_H$1) that form a pair of antigen binding regions. Linear antibodies can be bispecific or monospecific, as described in Zapata et al., 1995, *Protein Eng.* 8(10):1057-1062.

A "humanized" antibody for the purposes herein is an immunoglobulin amino acid sequence variant or fragment thereof which is capable of binding to a predetermined antigen and which comprises a FR region having substantially the amino acid sequence of a human immunoglobulin and a CDR having substantially the amino acid sequence of a non-human immunoglobulin.

Generally, a humanized antibody has one or more amino acid residues introduced into it from a source which is non-human. These non-human amino acid residues are referred to herein as "import" residues, which are typically taken from an "import" antibody domain, particularly a variable domain. An import residue, sequence, or antibody has a desired affinity and/or specificity, or other desirable antibody biological activity as discussed herein.

In general, the humanized antibody will comprise substantially all of at least one, and typically two, variable domains in which all or substantially all of the CDR regions correspond to those of a non-human immunoglobulin and all or substantially all of the FR regions are those of a human immunoglobulin sequence from, e.g., a consensus or germline sequence. The humanized antibody optionally also will comprise at least a portion of an immunoglobulin Fc region, typically that of a human immunoglobulin. Ordinarily, the antibody will contain both the light chain variable region as well as the heavy chain variable region. The antibody also may include the $C_H1$, hinge (J), $C_H2$, $C_H3$, and/or $C_H4$ regions of the heavy chain, and the $C_L$ region of the light chain, as appropriate.

The humanized antibody will be selected from any class of immunoglobulins, including IgM, IgG, IgD, IgA and IgE, and any isotype, including $IgG_1$, $IgG_2$, $IgG_3$ and $1gG_4$, and $IgA_1$, and $IgA_2$. The choice of which immunoglobulin class or isotype will depend, in part, on the desired effector function. For example, the ability of human immunoglobulins to mediate CDC and ADCC/ADCP is generally in the order of $IgM \approx IgG_1 \approx IgG_3 > IgG_2 > IgG_4$ and $IgG_1 \approx IgG_3 > IgG_2/IgM/IgG_4$, respectively. The humanized antibody may comprise sequences from more than one class or isotype, and selecting particular constant domains to optimize desired effector functions is within the ordinary skill in the art.

The FRs and CDRs of the humanized antibody need not correspond precisely to the parental sequences, e.g., the import CDR or the consensus FR may be altered by substitution, insertion or deletion of at least one residue so that the CDR or FR residue at that site does not correspond to either the consensus or the import antibody. Typically, such changes will not be extensive. Usually, at least 75% of the humanized antibody residues will correspond to those of the parental FR and CDR sequences, more often 90%, more often at least 95%, or at least 99%.

A "therapeutic agent" is an agent that exerts a cytotoxic, cytostatic, or immunomodulatory effect on cancer cells or activated immune cells. Examples of therapeutic agents include cytotoxic agents, chemotherapeutic agents, cytostatic agents, and immunomodulatory agents. Illustrative therapeutic agents include chemotherapeutic drugs, cytotoxins, immunomodulators, chelators, boron compounds, photoactive agents, photoactive dyes, steroids, radioisotopes, and the like.

An "immunoconjugate" is a conjugate of an antibody component with a therapeutic agent or a detectable label. Examples of conjugation of a therapeutic to an antibody are described in U.S. Pat. No. 6,884,869 and U.S. Published Application No. 2005-0238649, both of which are incorporated herein by reference in their entirety.

A "chemotherapeutic agent" is a chemical compound useful in the treatment of cancer. Examples of chemotherapeutic agents include alkylating agents such a thiotepa and cyclosphosphamide (CYTOXAN™); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues); cryptophycines (particularly cryptophycin 1 and cryptophycin 8); dolastatins, auristatins, (including analogues monomethyl-auristatin E and monomethyl-auristatin F described in US Published Application No. 2005-0238649, incorporated herein in its entirety); duocarmycins (including the synthetic analogues, KW-2189 and CBI-TMI); eleutherobin; pancratistatin; sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g. calicheamicin, especially calichemicin gammal I and calicheamicin phiI1, see for example, Agnew, 1994. *Chem. Intl. Ed. Engl.*, 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicins (e.g., Adriamycin™ Pharmacia S.p.A, Milan, Italy) (including morpholino-doxorubicin, cyanomorpholino-doxorubicin, 2-pyrrolino-doxorubicin, and deoxy-doxorubicin), epirubucin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, testolactone; anti-adranals such as amino glutethimide, mitotane, and trilostane; folic acid replenishers such as frolinic acid; aceglatone; aldophosphamide glycoside; aminolevulinic acid; eniluracil; amsacrine; bestrabucil; bisantrene; edatraxate; defofamine; democolcine; diaziquone; elformithine; elliptinium acetate; epothilones and analogs thereof; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine (Gemzar™, Eli Lilly and Co., Indianapolis, Ind.); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine™, GlaxoSmithKline, Research Triangle Park, N.C.); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™, AstraZeneca Pharmaceuticals), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above.

The term "prodrug" as used herein refers to a precursor or derivative form of a pharmaceutically active substance that is less cytotoxic to tumor cells compared to the parent drug and is capable of being enzymatically activated or converted into the more active parent form. See, for example, Wilman, 1986, "Prodrugs in Cancer Chemotherapy", In *Biochemical Society Transactions,* 14, pp. 375-382, 615th Meeting; and Belfast and Stella et al., 1985, "Prodrugs: A Chemical Approach to Targeted Drug Delivery", In: "*Directed Drug Delivery*, Borchardt et al., (ed.), pp. 247-267, Humana Press. Useful prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, and optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form include, but are not limited to, those chemotherapeutic agents described above.

A "cytotoxic effect" refers to the depletion, elimination and/or the killing of a target cell(s). A "cytotoxic agent" refers to an agent that has a cytotoxic effect on a cell. The term is intended to include radioactive isotopes (e.g., $I^{131}$, $I^{125}$, Y and $Re^{186}$), chemotherapeutic agents, and toxins such as enzymatically active toxins of bacterial, fungal, plant, or animal origin, and fragments thereof. Such cytotoxic agents can be coupled to a CD30 binding agent, e.g., a humanized anti-CD30 antibody, using known, standard procedures, and used, for example, to treat a subject indicated for therapy with the antibody. In one embodiment, "cytotoxic agent" is intended to include monoclonal antibodies, e.g. antibodies used in combination with the CD30 binding agents described herein. In some embodiments, a cytotoxic agent is not a radioisotope.

A "cytostatic effect" refers to the inhibition of cell proliferation. A "cytostatic agent" refers to an agent that has a cytostatic effect on a cell, thereby inhibiting the growth and/or expansion of a specific subset of cells.

The term "immunomodulatory effect" as used herein refers to a modulation of an immunologic response (e.g., its development or maintenance). Such modulation can be effected by, for example, elimination of immune cells (e.g., T or B lymphocytes); induction or generation of immune cells that can modulate (e.g., down-regulate) the functional capacity of other cells; induction of an unresponsive state in immune cells (e.g., anergy); or increasing, decreasing or changing the activity or function of immune cells, including, for example, altering the pattern of proteins expressed by these cells (e.g., altered production and/or secretion of certain classes of molecules such as cytokines, chemokines, growth factors, transcription factors, kinases, costimulatory molecules or other cell surface receptors, and the like).

The term "immunomodulatory agent" as used herein refers to an agent that modifies an immunologic response (e.g., its development or maintenance). Such modification can be effected by, for example, elimination of immune cells (e.g., T or B lymphocytes); induction or generation of immune cells that can modulate (e.g., down-regulate) the functional capacity of other cells; induction of an unresponsive state in immune cells (e.g., anergy); or increasing, decreasing or changing the activity or function of immune cells, including, for example, altering the pattern of proteins expressed by these cells (e.g., altered production and/or secretion of certain classes of molecules such as cytokines, chemokines, growth factors, transcription factors, kinases, costimulatory molecules or other cell surface receptors, and the like). In some embodiments, an immunomodulatory agent has a cytotoxic or cytostatic effect on an immune cell that promotes an immunologic response.

The term "label" refers to a detectable compound or composition that is conjugated directly or indirectly to a binding agent (e.g., an antibody). The label may itself be detectable (e.g., a radioisotope label or a fluorescent label) or, in the case of an enzymatic label, may catalyze a chemical alteration of a substrate compound or composition that is detectable. Labeled CD30 binding agents can be prepared and used in various applications including in vitro and in vivo diagnostics.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "control sequence" refers to a polynucleotide sequence necessary for expression of an operably linked coding sequence in a particular host organism. The control sequences suitable for use in prokaryotic cells include, for example, a promoter, operator and ribosome binding site sequences. Eukaryotic control sequences include, but are not limited to, promoters, polyadenylation signals, and enhancers. These control sequences can be utilized for expression and production of CD30 binding agents in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader, contiguous and in reading frame. However, enhancers are optionally contiguous. Linking can be accomplished, for example, by ligation at convenient restriction sites. If such sites do not exist, synthetic oligonucleotide adaptors, linkers or other methods known in the art can be used.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more complementarity determining regions (CDRs)). The term "fragment" refers to a portion of a polypeptide typically having at least 20 contiguous or at least 50 contiguous amino acids of the polypeptide.

A "derivative" is a polypeptide or fragment thereof having one or more non-conservative or conservative amino acid substitutions relative to a second polypeptide (also referred to as a "variant"; or a polypeptide or fragment thereof that is modified by covalent attachment of a second molecule such as, e.g., by attachment of a heterologous polypeptide, or by glycosylation, acetylation, phosphorylation, and the like. Further included within the definition of "derivative" are, for example, polypeptides containing one or more analogs of an amino acid (e.g., unnatural amino acids and the like), polypeptides with unsubstituted linkages, as well as other modifications known in the art, both naturally and non-naturally occurring.

An "isolated" polypeptide is one which has been identified and separated and/or recovered from a component of its natural environment. Contaminant components of its natural environment are materials which would interfere with diagnostic or therapeutic uses for the polypeptide, and may include enzymes, hormones, and other proteinaceous or nonproteinaceous solutes. An isolated polypeptide includes an isolated antibody, or a fragment or derivative thereof.

In certain embodiments, the polypeptide will be purified (1) to greater than 95% by weight of polypeptide as determined by the Lowry method, and in other aspects to more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. "Isolated antibody" includes the antibody in situ within recombinant cells since at least one component of the antibody's natural environment will not be present.

The term "heterologous," in the context of a polypeptide, means from a different source (e.g., a cell, tissue, organism, or species) as compared with another polypeptide, so that the two polypeptides are different. Typically, a heterologous polypeptide is from a different species.

In the context of immunoglobulin polypeptides, or fragments thereof, as defined above, "conservative substitution" means one or more amino acid substitutions that do not substantially reduce specific binding (e.g., as measured by the $K_D$) of the immunoglobulin polypeptide or fragment thereof to an antigen (e.g., substitutions that increase binding, that do not significantly alter binding, or that reduce binding by no more than about 40%, typically no more than about 30%, more typically no more than about 20%, even more typically no more than about 10%, or most typically no more than about 5%, as determined by standard binding assays such as, e.g., ELISA).

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences are the same length.

The term "substantially identical," in the context of two nucleic acids or polypeptides, refers to two or more sequences or subsequences that have at least 50%, at least 55%, at least 60%, or at least 65% identity; typically at least 70% or at least 75% identity; more typically at least 80% or at least 85% identity; and even more typically at least 90%, at least 95%, at least 98% identity, or at least 99% identity (e.g., as determined using one of the methods set forth infra).

The terms "similarity" or "percent similarity" in the context of two or more polypeptide sequences, refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or 95% identical, or conservatively substituted, to the second amino acid sequence when compared to an equal number of amino acids as the number contained in the first sequence, or when compared to an alignment of polypeptides that has been aligned by, for example, one of the methods set forth infra.

The terms "substantial similarity" or "substantially similar," in the context of polypeptide sequences, indicates that a polypeptide region has a sequence with at least 70%, typically at least 80%, more typically at least 85%, or at least 90% or at least 95% sequence similarity to a reference sequence. For example, a polypeptide is substantially similar to a second polypeptide, for example, where the two peptides differ by one or more conservative substitutions.

In the context of CD30 binding agents, a protein that has one or more polypeptide regions substantially identical or substantially similar to one or more antigen-binding regions (e.g., a heavy or light chain variable region, or a heavy or light chain CDR) of an anti-CD30 antibody retains specific binding to an epitope of CD30 recognized by the anti-CD30 antibody, as determined using any of various standard immunoassays known in the art or as referred to herein.

The determination of percent identity or percent similarity between two sequences can be accomplished using a mathematical algorithm. A non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and) (BLAST programs of Altschul et al., 1990, *J. Mol. Biol.* 215:403-410. BLAST nucleotide searches can be performed with the NBLAST program, score=100, wordlength=12, to obtain nucleotide sequences homologous to a nucleic acid encoding a protein of interest. BLAST protein searches can be performed with the) (BLAST program, score=50, wordlength=3, to obtain amino acid sequences homologous to a protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perfoini an iterated search which detects distant relationships between molecules (id.). When utilizing BLAST, Gapped BLAST, and PSI-BLAST programs, the default parameters of the respective programs (e.g.,) (BLAST and NBLAST) can be used. Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, *Methods Enzymol.* 266:383-402.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers. It is also understood that all progeny may not be precisely identical in DNA content, due to deliberate or naturally occurring mutations. Mutant progeny that have the same function or biological activity as screened for in the originally transformed cell are included. Where distinct designations are intended, it will be clear from the context.

"Immune cell" as used herein refers to a cell of hematopoietic lineage involved in regulating an immune response. In typical embodiments, an immune cell is a T lymphocyte, a B lymphocyte, an NK cell, a monocyte/macrophage or a dendritic cell.

"Effector cell" as used herein refers to a cell that expresses a surface receptor for the Fc region of an immunoglobulin (FcR). For example, cells that express surface FcR for IgGs including FcγRIII (CD16), FcγRII (CD32) and FcγRI (CD64) can act as effector cells. Such effector cells include monocytes, macrophages, natural killer (NK) cells, neutrophils and eosinophils.

The term "antibody effector function(s)" as used herein refers to a function contributed by an Fc region(s) of an Ig. Such function can be effected by, for example, binding of an Fc effector region(s) to an Fc receptor on an immune cell with phagocytic or lytic activity or by binding of an Fc effector region(s) to components of the complement system. Typically, the effect(s) mediated by the Fc-binding cells or complement components result in inhibition and/or depletion of the CD30-expressing target cell.

A "disorder", as used herein, and the terms "CD30-associated disorder" and "CD30-associated disease" refer to any condition that would benefit from treatment with a CD30 binding agent described herein. This includes chronic and acute disorders or diseases including those pathological conditions that predispose the mammal to the disorder in question. Non-limiting examples or disorders to be treated herein include cancer, hematological malignancies, benign and malignant tumors, leukemias and lymphoid malignancies, carcinomas, and inflammatory, angiogenic and immunologic disorders. Specific examples of disorders are disclosed infra.

The terms "treatment" and "therapy", and the like, as used herein, are meant to include therapeutic or suppressive measures for a disease or disorder leading to any clinically desirable or beneficial effect, including, but not limited to, alleviation or relief of one or more symptoms, regression, slowing or cessation of progression of the disease or disorder associated with CD30 expression, such as a cancer or an immunological disorder. For example, treatment can include a decrease or elimination of a clinical or diagnostic symptom of a CD30-expressing disorder after the onset of the clinical or diagnostic symptom by administration of an anti-CD30 antibody or other CD30 binding agent to a subject. Treatment can be evidenced as a decrease in the severity of a symptom, the number of symptoms, or frequency of relapse.

The term "intravenous infusion" refers to introduction of an agent, e.g., a CD30 binding agent, into the vein of an animal or human subject over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent, e.g., a CD30 binding agent, under the skin of an animal or human subject, typically within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human subject, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human subject, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human subject, where bolus drug delivery is less than approximately 15 minutes, less than 5 minutes or less than 60 seconds. Administration can be, for example, within a pocket between the skin and underlying tissue, where the pocket may be created by pinching or drawing the skin up and away from underlying tissue.

The term "package insert" is used to refer to instructions customarily included in commercial packages of therapeutic products, that contain information about the indications, usage, usage, administration, contraindications and/or warnings concerning the use of such therapeutic products.

The term "effective amount" refers to the amount of an antibody or other CD30 binding agent that is sufficient to inhibit the occurrence or ameliorate one or more clinical or diagnostic symptoms of a CD30-expressing cancer or immunological disorder in a subject. An effective amount of an agent is administered according to the methods described herein in an "effective regimen." The term "effective regimen" refers to a combination of amount of the agent and dosage frequency adequate to accomplish treatment or prevention of a CD30-expressing cancer or immunological disorder.

The term "pharmaceutically acceptable" as used herein means approved by a regulatory agency of the Federal or a state government or listed in the U.S. Pharmacopeia or other generally recognized pharmacopeia for use in animals, and more particularly in humans.

The term "pharmaceutically compatible ingredient" refers to a pharmaceutically acceptable diluent, adjuvant, excipient, or vehicle with which a CD30 binding agent is administered.

The phrase "pharmaceutically acceptable salt," as used herein, refers to pharmaceutically acceptable organic or inorganic salts of an anti-CD30 binding agent or therapeutic agent. The anti-CD30 binding agent or therapeutic agent contains at least one amino group, and accordingly acid addition salts can be formed with this amino group or other suitable groups. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The term "pharmaceutically acceptable solvate" or "solvate" refers to an association of one or more solvent molecules and an anti-CD30 binding agent and/or therapeutic agent. Examples of solvents that form pharmaceutically acceptable solvates include, but are not limited to, water, isopropanol, ethanol, methanol, DMSO, ethyl acetate, acetic acid, and ethanolamine.

The abbreviation "AFP" refers to dimethylvaline-valine-dolaisoleuine-dolaproine-phenylalanine-p-phenylenediamine.

The abbreviation "MMAE" refers to monomethyl auristatin E.

The abbreviation "AEB" refers to an ester produced by reacting auristatin E with paraacetyl benzoic acid.

The abbreviation "AEVB" refers to an ester produced by reacting auristatin E with benzoylvaleric acid.

The abbreviation "MMAF" refers to dovaline-valine-dolaisoleuine-dolaproine-phenylalanine.

II. Anti-CD30 Binding Agents

The methods and compositions described herein encompass the use of CD30 binding agents that specifically bind to CD30 and exert a cytotoxic, cytostatic or immunomodulatory effect on CD30-expressing cancer cells or other target cells. The CD30 binding agent can be, for example, an anti-CD30 antibody, an antigen-binding fragment of an anti-CD30 antibody, a derivative thereof, or other CD30 binding agent comprising the amino acid sequence of a humanized antibody heavy and/or light chain variable region. The CD30 binding agent exerts a cytotoxic or cytostatic effect on CD30-expressing cancer cells, and/or exerts a cytotoxic, cytostatic, or immunomodulatory effect on cells of the immune sytem, such as activated lymphocytes or dendritic cells, in the treatment of a CD30-expressing cancer or an immunological disorder, respectively.

A CD30 binding agent can be, for example, an intact anti-CD30 antibody, such as a humanized antibody, or an antigen-binding fragment thereof, such as a single chain antibody; an scFv, a diabody, an Fab, a minibody, an scFv-Fc, an Fv, or the like. In one aspect, the CD30 binding agent comprises one or more complementarity determining regions (CDRs) identical, substantially identical or substantially similar to one or more CDR(s) of chimeric monoclonal antibody AC10 (cAC10). (The nucleic acid and amino acid sequences of the heavy and light chain variable regions of chimeric AC10 are of SEQ ID NO:1 and SEQ ID NO:2, and SEQ ID NO: 23 and SEQ ID NO: 24, respectively.) For example, the binding agent can include a heavy chain CDR and/or a light chain CDR that is identical, substantially identical or substantially similar to a corresponding heavy chain CDR (H1, H2, or H3 regions) or corresponding light chain CDR (L1, L2, or L3 regions) of mAb cAC10. In typical embodiments, the anti-CD30 binding agent has two or three heavy chain CDRs and/or two or three light chain CDRs that are identical, substantially identical or substantially similar to corresponding heavy and/or light chain CDRs of mAb cAC10.

For example, in some embodiments, where the anti-CD30 binding agent has at least one heavy chain CDR identical, substantially identical or substantially similar to a heavy chain CDR of mAb cAC10, the binding agent can further include at least one light chain CDR that is identical, substantially identical or substantially similar to a light chain CDR of mAb cAC10.

In some embodiments, the anti-CD30 binding agent includes a heavy or light chain variable domain, the variable domain having (a) a set of three CDRs identical, substantially identical or substantially similar to the corresponding CDRs of mAb cAC10, and (b) a set of four variable region framework regions from a human immunoglobulin. For example, an anti-CD30 binding agent, such as an antibody, can include a heavy and/or light chain variable domain(s), the variable domain(s) having (a) a set of three CDRs, in which the set of CDRs are from mAb cAC10, and (b) a set of four framework regions derived from a human IgG. The antibody can optionally include a hinge region. In an exemplary embodiment, the anti-CD30 binding agent is a fully humanized antibody.

In some embodiments, the framework regions are chosen from human germline exon $V_H$, $J_H$, Vκ and Jκ sequences. For example, acceptor sequences for humanization of FR regions of the mAb cAC10 $V_H$ domain can be selected from germline $V_H$ exons $V_H$1-18 (Matsuda et al., 1993, *Nature Genetics* 3:88-94) or $V_H$1-2 (Shin et al., 1991, *EMBO J.* 10:3641-3645) and for the hinge region ($J_H$), exon $J_H$-6 (Mattila et al., 1995, *Eur. J. Immunol.* 25:2578-2582). In other examples, germline Vκ exon B3 (Cox et al., 1994, *Eur. J. Immunol.* 24:827-836) or Jκ exon Jκ-1 (Hieter et al., 1982, *J. Biol. Chem.* 257:1516-1522) can be selected as acceptor sequences for cAC10 $V_L$ domain humanization.

In some embodiments, the sequence of the framework region of the CD30 binding agent includes a derivative (e.g., a variant) of the acceptor human germline exon used, such as a derivative in which mouse donor residues are reintroduced. Such residues can include reintroduction of the mouse donor residue at one or more of positions H71 and H91 in the $V_H$ domain, and/or L25 and/or L33 in the $V_L$ domain, according to the Kabat numbering convention (1991, NIH Publ. No. 91-3242, Vol. I, pages 647-669).

In some embodiments, the CD30 binding agent comprises a heavy chain variable region comprising the germline $V_H$ exons $V_H$1-18 (Matsuda et al., 1993, *Nature Genetics* 3:88-94) or $V_H$1-2 (Shin et al., 1991, *EMBO J.* 10:3641-3645) and for the hinge region ($J_H$), exon $J_H$-6 (Mattila et al., 1995, *Eur. J. Immunol.* 25:2578-2582). The heavy chain variable region further comprises CDR-H1 (about residues 31-35), CDR-H2 (about residues 50-65), and/or CDR-H3 (about residues 95-102) or a sequence at least 85%, at least 90% or at least 95% identifical to CDR-H1, CDR-H2 and/or CDR-H3, according to the Kabat numbering convention.

In some embodiments, the CD30 binding agent comprises a light chain variable region comprising the germane Vκ exon B3 (Cox et al., 1994, *Eur. J. Immunol.* 24:827-836) or Jκ exon Jκ-1 (Hieter et al., 1982, *J. Biol. Chem.* 257:1516-1522). The light chain variable region further comprises CDR-L1 (about residues 24-34), CDR-L2 (about residues 50-56), and/or CDR-L3 (about residues 89-97) or a sequence at least 85%, at least 90% or at least 95% identical to CDR-L1, CDR-L2 and/or CDR-L3, according to the Kabat numbering convention.

The following table provides a summary of the regions of chimeric and humanized AC10 to which each sequence identifier (SEQ ID NO.) corresponds.

TABLE 1

| MOLECULE | NUCLEOTIDE OR AMINO ACID | SEQ ID NO |
|---|---|---|
| cAC10 Heavy Chain Variable Region | Nucleotide | 1 |
| cAC10 Heavy Chain Variable Region | Amino Acid | 2 |
| hAC10 hV$_H$A | Nucleotide | 3 |
| hAC10 hV$_H$A | Amino Acid | 4 |
| Leader + hAC10 hV$_H$A + hIgG$_1$ Constant Domain | Nucleotide | 5 |
| Leader + hAC10 hV$_H$A + hIgG$_1$ Constant Domain | Amino Acid | 6 |
| hAC10 hV$_H$A + hIgG$_1$ Constant Domain | Amino Acid | 7 |
| hAC10 hV$_H$B | Nucleotide | 8 |
| hAC10 hV$_H$B | Amino Acid | 9 |
| Leader + hAC10 hV$_H$B + hIgG$_1$ Constant Domain | Nucleotide | 10 |
| Leader + hAC10 hV$_H$B + hIgG$_1$ Constant Domain | Amino Acid | 11 |
| hAC10 hV$_H$B + hIgG$_1$ Constant Domain | Amino Acid | 12 |
| hAC10 hV$_H$C | Nucleotide | 13 |
| hAC10 hV$_H$C | Amino Acid | 14 |
| Leader + hAC10 hV$_H$C + hIgG$_1$ Constant Domain | Nucleotide | 15 |
| Leader + hAC10 hV$_H$C + hIgG$_1$ Constant Domain | Amino Acid | 16 |
| hAC10 hV$_H$C + hIgG$_1$ Constant Domain | Amino Acid | 17 |
| hAC10 hV$_H$D | Nucleotide | 18 |
| hAC10 hV$_H$D | Amino Acid | 19 |
| Leader + hAC10 hV$_H$D + hIgG$_1$ Constant Domain | Nucleotide | 20 |
| Leader + hAC10 hV$_H$D + hIgG$_1$ Constant Domain | Amino Acid | 21 |
| hAC10 hV$_H$D + hIgG$_1$ Constant Domain | Amino Acid | 22 |
| cAC10 Light Chain Variable Region | Nucleotide | 23 |
| cAC10 Light Chain Variable Region | Amino Acid | 24 |
| hV$_L$A | Nucleotide | 25 |
| hV$_L$A | Amino Acid | 26 |
| Leader + hV$_L$A + human κ constant domain | Nucleotide | 27 |
| Leader + hV$_L$A + human κ constant domain | Amino Acid | 28 |
| hV$_L$A + human κ constant domain | Amino Acid | 29 |
| hV$_L$B | Nucleotide | 30 |
| hV$_L$B | Amino Acid | 31 |
| Leader + hV$_L$B + human κ constant domain | Nucleotide | 32 |
| Leader + hV$_L$B + human κ constant domain | Amino Acid | 33 |
| hV$_L$B + human κ constant domain | Amino Acid | 34 |
| hV$_L$C | Nucleotide | 35 |
| hV$_L$C | Amino Acid | 36 |
| Leader + hV$_L$C + human κ constant domain | Nucleotide | 37 |
| Leader + hV$_L$C + human κ constant domain | Amino Acid | 38 |
| hV$_L$C + human κ constant domain | Amino Acid | 39 |
| hV$_L$D | Nucleotide | 40 |
| hV$_L$D | Amino Acid | 41 |
| Leader + hV$_L$D + human κ constant domain | Nucleotide | 42 |
| Leader + hV$_L$D + human κ constant domain | Amino Acid | 43 |
| hV$_L$D + human κ constant domain | Amino Acid | 44 |

In some embodiments, the CD30 binding agent is a fully humanized antibody or antigen-binding fragment of mAb cAC10. In some embodiments, the antibody comprises a polypeptide chain having the amino acid sequence of SEQ ID NO:6, SEQ ID NO:7, SEQ ID NO:11, SEQ ID NO:12, SEQ ID NO:16, SEQ ID NO:17, SEQ ID NO:21 or SEQ ID NO:22. In some embodiments, the antibody comprises a polypeptide chain having the amino acid sequence of SEQ ID NO:28, SEQ ID NO:29, SEQ ID NO:33, SEQ ID NO:34, SEQ ID NO:38, SEQ ID NO:39, SEQ ID NO:43 or SEQ ID NO:44.

In some embodiments, the antibody or antigen-binding fragment comprises a polypeptide chain that is at least 80% identical to the amino acid sequence of SEQ ID NO:4, SEQ ID NO:9, SEQ ID NO:14 or SEQ ID NO:19. In some embodiments, the antibody or antigen-binding fragment comprises a polypeptide chain that is at least 85% identical to the amino acid sequence of SEQ ID NO:4, SEQ ID NO:9, SEQ ID NO:14 or SEQ ID NO:19. In some embodiments, the antibody or antigen-binding fragment comprises a polypeptide chain that is at least 90% identical to the amino acid sequence of SEQ ID NO:4, SEQ ID NO:9, SEQ ID NO:14 or SEQ ID NO:19. In some embodiments, the antibody or antigen-binding fragment comprises a polypeptide chain that is at least 95% identical to the amino acid sequence of SEQ ID NO:4, SEQ ID NO:9, SEQ ID NO:14 or SEQ ID NO:19. In some embodiments, the antibody or antigen-binding fragment comprises a polypeptide chain that is at least 99% identical to the amino acid sequence of SEQ ID NO:4, SEQ ID NO:9, SEQ ID NO:14 or SEQ ID NO:19. In some embodiments, the antibody or antigen-binding fragment comprises a polypeptide chain that is identical to the amino acid sequence of SEQ ID NO:4, SEQ ID NO:9, SEQ ID NO:14 or SEQ ID NO:19. In some embodiments, the antibody does not have the amino acid sequence of the heavy chain variable region of mAb AC10 or cAC10.

In some embodiments, the antibody or antigen-binding fragment comprises a polypeptide chain that is at least 80% identical to the amino acid sequence of SEQ ID NO:26, SEQ ID NO:31, SEQ ID NO:36 or SEQ ID NO:41. In some embodiments, the antibody or antigen-binding fragment comprises a polypeptide chain that is at least 85% identical to the amino acid sequence of SEQ ID NO:26, SEQ ID NO:31, SEQ ID NO:36 or SEQ ID NO:41. In some embodiments, the antibody or antigen-binding fragment comprises a polypeptide chain that is at least 90% identical to the amino acid sequence of SEQ ID NO:26, SEQ ID NO:31, SEQ ID NO:36 or SEQ ID NO:41. In some embodiments, the antibody or antigen-binding fragment comprises a polypeptide chain that is at least 95% identical to the amino acid sequence of SEQ ID NO:26, SEQ ID NO:31, SEQ ID NO:36 or SEQ ID NO:41. In some embodiments, the antibody or antigen-binding fragment comprises a polypeptide chain that is at least 99% identical to the amino acid sequence of SEQ ID NO:26, SEQ ID NO:31, SEQ ID NO:36 or SEQ ID NO:41. In some embodiments, the antibody or antigen-binding fragment comprises a polypeptide chain that is identical to the amino acid sequence of SEQ ID NO:26, SEQ ID NO:31, SEQ ID NO:36 or SEQ ID NO:41. In some embodiments, the antibody does not have the amino acid sequence of the heavy chain variable region of mAb AC10 or cAC10.

In some embodiments, the antibody or antigen-binding fragment comprises a polypeptide chain that is at least 80% identical to the amino acid sequence of SEQ ID NO:7, SEQ ID NO:12, SEQ ID NO:17 or SEQ ID NO:22. In some embodiments, the antibody or antigen-binding fragment comprises a polypeptide chain that is at least 85% identical to the amino acid sequence of SEQ ID NO:7, SEQ ID NO:12, SEQ ID NO:17 or SEQ ID NO:22. In some embodiments, the antibody or antigen-binding fragment comprises a polypeptide chain that is at least 90% identical to the amino acid sequence of SEQ ID NO:7, SEQ ID NO:12, SEQ ID NO:17 or SEQ ID NO:22. In some embodiments, the antibody or antigen-binding fragment comprises a polypeptide chain that is at least 95% identical to the amino acid sequence of SEQ ID NO:7, SEQ ID NO:12, SEQ ID NO:17 or SEQ ID NO:22. In some embodiments, the antibody or antigen-binding fragment comprises a polypeptide chain that is at least 99% identical to the amino acid sequence of SEQ ID NO:7, SEQ ID NO:12, SEQ ID NO:17 or SEQ ID NO:22. In some embodiments, the antibody or antigen-binding fragment comprises a polypeptide chain that is identical to the amino acid sequence of SEQ ID NO:7, SEQ ID NO:12, SEQ ID NO:17 or SEQ ID NO:22. In some embodiments, the antibody does not have the amino acid sequence of the heavy chain variable region of mAb AC10 or cAC10.

In some embodiments, the antibody or antigen-binding fragment comprises a polypeptide chain that is at least 80% identical to the amino acid sequence of SEQ ID NO:29, SEQ ID NO:34, SEQ ID NO:39 or SEQ ID NO:44. In some embodiments, the antibody or antigen-binding fragment comprises a polypeptide chain that is at least 85% identical to the amino acid sequence of SEQ ID NO:29, SEQ ID NO:34, SEQ ID NO:39 or SEQ ID NO:44. In some embodiments, the antibody or antigen-binding fragment comprises a polypeptide chain that is at least 90% identical to the amino acid sequence of SEQ ID NO:29, SEQ ID NO:34, SEQ ID NO:39 or SEQ ID NO:44. In some embodiments, the antibody or antigen-binding fragment comprises a polypeptide chain that is at least 95% identical to the amino acid sequence of SEQ ID NO:29, SEQ ID NO:34, SEQ ID NO:39 or SEQ ID NO:44. In some embodiments, the antibody or antigen-binding fragment comprises a polypeptide chain that is at least 99% identical to the amino acid sequence of SEQ ID NO:29, SEQ ID NO:34, SEQ ID NO:39 or SEQ ID NO:44. In some embodiments, the antibody or antigen-binding fragment comprises a polypeptide chain that identical to the amino acid sequence of SEQ ID NO:29, SEQ ID NO:34, SEQ ID NO:39 or SEQ ID NO:44. In some embodiments, the antibody does not have the amino acid sequence of the light chain variable region of mAb AC10 or cAC10.

In some embodiments, the CD30 binding agent competes with monoclonal antibody AC10 or chimeric AC10 for binding to human CD30. In some embodiments, the CD30 binding agent can trigger apoptosis and/or growth inhibition pathways upon binding to CD30 on a target cell (e.g., p21 induction, cell cycle arrest) and produce DNA fragmentation. (See, e.g., Cerveny et al., 2005, *Leukemia* 19:1648-1655, and Wahl et al., 2002, *Cancer Res.* 62:3736-3742, each of which is hereby incorporated by reference in its entirety.) In some embodiments, the CD30 binding agent induces a cytotoxic, cytostatic or immunomodulatory effect in the absence of effector cells. In other embodiments, the CD30 binding agent does not induce an agonistic or antagonistic signal when bound to CD30.

The CD30 binding agent can optionally include an antibody effector region that mediates or stimulates an ADCC, ADCP and/or CDC response against a CD30-expressing target cell. The effector domain(s) can be, for example, an Fc region such as a hinge-$C_H2$-$C_H3$ region of an immunoglobulin, or a portion or fragment of an effector region having effector function. Antigen-binding antibody fragments, including single-chain antibodies, can comprise, for example, the variable region(s) in combination with the entirety or a portion of an effector region (e.g., a $C_H2$ and/or $C_H3$ domain alone or in combination with a $C_H1$, hinge and/or $C_L$ domain). Also, antigen-binding fragments can comprise any combination of effector regions. In some embodiments, the anti-CD30 antibody can be a single chain antibody comprising a CD30-binding variable region joined to hinge-$C_H2$-$C_H3$ domains.

Such a CD30 binding agent can exert a cytotoxic or cytostatic effect on CD30-expressing cancer cells, or exert a cytotoxic, cytostatic, or immunomodulatory effect on activated lymphocytes or dendritic cells, for example, in the treatment of a CD30-expressing cancer or an immunological disorder, respectively. Typically, the CD30 binding agent recruits and/or activates cytotoxic white blood cells (e.g., natural killer (NK) cells, phagocytotic cells (e.g., macrophages), and/or serum complement components).

The effector region of the anti-CD30 antibody can be from any suitable immunoglobulin isotype. For example, the ability of human immunoglobulin to mediate CDC and ADCC/ADCP is generally in the order of $IgM \approx IgG_1 \approx IgG_3 > IgG_2 > IgG_4$ and $IgG_1 \approx IgG_3 > IgG_2 / IgM / IgG_4$, respectively. A CD30 binding agent can be expressed as a recombinant fusion protein comprising of the appropriate constant domains to yield the desired effector function(s). Upon binding to target cells, the CD30 binding agent can trigger in vitro and in vivo target cell destruction through an antibody effector function, such as ADCC, CDC, and/or ADCP.

In some embodiments, the CD30 binding agent does not include an effector region that can functionally interact with and activate cytotoxic white blood cells and/or serum complement components.

The CD30 binding agent optionally can be conjugated to a therapeutic agent, such as a cytotoxic, cytostatic or immunomodulatory agent. Suitable therapeutic agents are described herein.

In some embodiments, a CD30 binding agent can be a chimeric anti-CD30 antibody, comprising a human or non-human Fc region or portion thereof. For example, the antibody can include an Fc region or portion thereof of non-human origin, e.g., rodent (e.g., mouse or rat), donkey, sheep, rabbit, goat, guinea pig, camelid, horse, chicken or monkey (e.g., macaque, rhesus, cynomolgous or the like) linked to humanized heavy and/or light chain variable regions.

A CD30 binding agent, such as an antibody, can be mono-specific, bispecific, trispecific, or of greater multispecificity. Multispecific antibodies may be specific for different epitopes of CD30 and/or may be specific for both CD30 as well as for a heterologous protein. (See, e.g., PCT Publications WO 93/17715, WO 92/08802, WO 91/00360, and WO 92/05793; Tutt et al., 1991, *J. Immunol.* 147:60-69; U.S. Pat. Nos. 4,474,893; 4,714,681; 4,925,648; 5,573,920; and 5,601,819; Kostelny et al., 1992, *J. Immunol.* 148:1547-1553.) Multispecific antibodies, including bispecific and trispecific antibodies, useful for practicing the methods described herein are antibodies that immunospecifically bind to both CD30 (including but not limited to antibodies that have the CDRs of the monoclonal antibody AC10) and a second cell surface receptor or receptor complex that mediates ADCC, ADCP, and/or CDC, such as CD16/FcγRIII, CD64/FcγRI, killer inhibitory or activating receptors, or the complement control protein CD59. In a typical embodiment, the binding of the multispecific antibody to the second cell surface molecule or receptor complex enhances the effector functions of the anti-CD30 antibody or other CD30 binding agent.

Anti-CD30 binding agents may also be described or specified in terms of their binding affinity to CD30. Typical binding affinities include those with a dissociation constant or Kd less than $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In another aspect, nucleic acids encoding a CD30 binding agent are provided. In some embodiments, the CD30 binding agent can be a fully humanized antibody or a humanized antigen-binding fragment of mAb cAC10. In some embodiments, the nucleic acid encodes a polypeptide chain having the amino acid sequence of SEQ ID NO:6, SEQ ID NO:7, SEQ ID NO:11, SEQ ID NO:12, SEQ ID NO:16, SEQ ID NO:17, SEQ ID NO:21 or SEQ ID NO:22. In some embodiments, the nucleic acid encodes a polypeptide chain having the amino acid sequence of SEQ ID NO:28, SEQ ID NO:29, SEQ ID NO:33, SEQ ID NO:34, SEQ ID NO:38, SEQ ID NO:39, SEQ ID NO:43 or SEQ ID NO:44.

In some embodiments, the nucleic acid encodes a polypeptide chain that is at least 80% identical to the amino acid sequence of SEQ ID NO:4, SEQ ID NO:9, SEQ ID NO:14 or SEQ ID NO:19. In some embodiments, the nucleic acid encodes a polypeptide chain that is at least 85% identical to the amino acid sequence of SEQ ID NO:4, SEQ ID NO:9, SEQ ID NO:14 or SEQ ID NO:19. In some embodiments, the nucleic acid encodes a polypeptide chain that is at least 90% identical to the amino acid sequence of SEQ ID NO:4, SEQ ID NO:9, SEQ ID NO:14 or SEQ ID NO:19. In some embodiments, the nucleic acid encodes a polypeptide chain that is at least 95% identical to the amino acid sequence of SEQ ID NO:4, SEQ ID NO:9, SEQ ID NO:14 or SEQ ID NO:19. In some embodiments, the nucleic acid encodes a polypeptide chain that is at least 99% identical to the amino acid sequence of SEQ ID NO:4, SEQ ID NO:9, SEQ ID NO:14 or SEQ ID NO:19. In some embodiments, the nucleic acid encodes a polypeptide chain that is identical to the amino acid sequence of SEQ ID NO:4, SEQ ID NO:9, SEQ ID NO:14 or SEQ ID NO:19. In some embodiments, the nucleic acid does not encode a polypeptide having the amino acid sequence of the heavy chain variable region of mAb AC10 or cAC10.

In some embodiments, the nucleic acid encodes a polypeptide chain that is at least 80% identical to the amino acid sequence of SEQ ID NO:26, SEQ ID NO:31, SEQ ID NO:36 or SEQ ID NO:41. In some embodiments, the nucleic acid encodes a polypeptide chain that is at least 85% identical to the amino acid sequence of SEQ ID NO:26, SEQ ID NO:31, SEQ ID NO:36 or SEQ ID NO:41. In some embodiments, the nucleic acid encodes a polypeptide chain that is at least 90% identical to the amino acid sequence of SEQ ID NO:26, SEQ ID NO:31, SEQ ID NO:36 or SEQ ID NO:41. In some embodiments, the nucleic acid encodes a polypeptide chain that is at least 95% identical to the amino acid sequence of SEQ ID NO:26, SEQ ID NO:31, SEQ ID NO:36 or SEQ ID NO:41. In some embodiments, the nucleic acid encodes a polypeptide chain that is at least 99% identical to the amino acid sequence of SEQ ID NO:26, SEQ ID NO:31, SEQ ID NO:36 or SEQ ID NO:41. In some embodiments, the nucleic acid encodes a polypeptide chain that is identical to the amino acid sequence of SEQ ID NO:26, SEQ ID NO:31, SEQ ID NO:36 or SEQ ID NO:41. In some embodiments, the nucleic acid does not encode a polypeptide having the amino acid sequence of the light chain variable region of mAb ACID or cAC10.

In some embodiments, the nucleic acid encodes a polypeptide chain that is at least 80% identical to the amino acid sequence of SEQ ID NO:7, SEQ ID NO:12, SEQ ID NO:17 or SEQ ID NO:22. In some embodiments, the nucleic acid encodes a polypeptide chain that is at least 85% identical to the amino acid sequence of SEQ ID NO:7, SEQ ID NO:12, SEQ ID NO:17 or SEQ ID NO:22. In some embodiments, the nucleic acid encodes a polypeptide chain that is at least 90% identical to the amino acid sequence of SEQ ID NO:7, SEQ ID NO:12, SEQ ID NO:17 or SEQ ID NO:22. In some embodiments, the nucleic acid encodes a polypeptide chain that is at least 95% identical to the amino acid sequence of SEQ ID NO:7, SEQ ID NO:12, SEQ ID NO:17 or SEQ ID NO:22. In some embodiments, the nucleic acid encodes a polypeptide chain that is at least 99% identical to the amino acid sequence of SEQ ID NO:7, SEQ ID NO:12, SEQ ID NO:17 or SEQ ID NO:22. In some embodiments, the nucleic acid encodes a polypeptide chain that is identical to the amino acid sequence of SEQ ID NO:7, SEQ ID NO:12, SEQ ID NO:17 or SEQ ID NO:22. In some embodiments, the nucleic acid does not encode a polypeptide having the amino acid sequence of the heavy chain variable region of mAb AC10 or cAC10.

In some embodiments, the nucleic acid encodes a polypeptide chain that is at least 80% identical to the amino acid sequence of SEQ ID NO:29, SEQ ID NO:34, SEQ ID NO:39 or SEQ ID NO:44. In some embodiments, the nucleic acid encodes a polypeptide chain that is at least 85% identical to the amino acid sequence of SEQ ID NO:29, SEQ ID NO:34, SEQ ID NO:39 or SEQ ID NO:44. In some embodiments, the nucleic acid encodes a polypeptide chain that is at least 90% identical to the amino acid sequence of SEQ ID NO:29, SEQ ID NO:34, SEQ ID NO:39 or SEQ ID NO:44. In some embodiments, the nucleic acid encodes a polypeptide chain that is at least 95% identical to the amino acid sequence of SEQ ID NO:29, SEQ ID NO:34, SEQ ID NO:39 or SEQ ID NO:44. In some embodiments, the nucleic acid encodes a polypeptide chain that is at least 99% identical to the amino acid sequence of SEQ ID NO:29, SEQ ID NO:34, SEQ ID NO:39 or SEQ ID NO:44. In some embodiments, the nucleic acid encodes a polypeptide chain that is identical to the amino acid sequence of SEQ ID NO:29, SEQ ID NO:34, SEQ ID NO:39 or SEQ ID NO:44. In some embodiments, the nucleic acid does not encode a polypeptide having the amino acid sequence of the light chain variable region of mAb AC10 or cAC10.

In some embodiments, the nucleic acid has the sequence of SEQ ID NO:3, SEQ ID NO:5, SEQ ID NO:8, SEQ NO:10, SEQ ID NO:13, SEQ ID NO:15, SEQ ID NO:18, SEQ ID NO:20, SEQ ID NO:23, SEQ ID NO:25, SEQ ID NO.: 27, SEQ ID NO:30, SEQ ID NO:32, SEQ ID NO:35, SEQ ID NO:37, SEQ ID NO:40, or SEQ ID NO:42, or the respective complement thereof.

Also included in some embodiments are nucleic acids encoding a CD30 binding agent that hybridize under low, moderate, and high stringency conditions, as defined herein, to all or a portion of a nucleotide sequence encoding a CD30 binding agent disclosed herein, or by its complement. For example, a nucleic acid can hybridize under low, moderate or high stringency conditions to a nucleic acid having the nucleotide sequence of, for example, SEQ ID NO:3, SEQ ID NO:5, SEQ ID NO:8, SEQ NO:10, SEQ ID NO:13, SEQ ID NO:15, SEQ ID NO:18, SEQ ID NO:20, SEQ ID NO:23, SEQ ID NO:25, SEQ ID NO:27, SEQ ID NO:30, SEQ ID NO:32, SEQ ID NO:35, SEQ ID NO:37, SEQ ID NO:40, or SEQ ID NO:42, or the respective complement thereof. The hybridizing portion of the hybridizing nucleic acid is typically at least 15 (e.g., 20, 25, 30 or 50) nucleotides in length. In some embodiments, the hybridizing portion of the hybridizing nucleic acid is at least 80%, at least 90%, at least 95%, at least 98%, or at least 99% identical to the sequence of a portion or all of a nucleic acid encoding the anti-CD30 binding agent, or its complement. Hybridizing nucleic acids of the type described herein can be used, for example, as a cloning probe or a primer, e.g., a PCR primer.

CD30 binding agents can be generated by methods known in the art. For example, monoclonal antibodies can be prepared using a wide variety of techniques including, e.g., the use of hybridoma, recombinant, and phage display technologies, or a combination thereof. Hybridoma techniques are generally discussed in, for example, Harlow et al., *Antibodies: A Laboratory Manual* (Cold Spring Harbor Laboratory Press, 2nd ed., 1988; Harlow and Lane, *Using Antibodies, A Laboratory Manual*, Cold Spring Harbor Laboratory, New York (1999); and Hammerling et al., In *Monoclonal Antibodies and T-Cell Hybridomas*, pp. 563-681 (Elsevier, N.Y., 1981). Examples of phage display methods that can be used to make anti-CD30 antibodies include, e.g., those disclosed in Hoogenboom and Winter, 1991, *J. Mol. Biol.* 227:381; Marks et al., 1991, *J. Mol. Biol.* 222:581; Quan and Carter, 2002, *The rise of monoclonal antibodies as therapeutics in Anti-IgE and Allergic Disease*, Tardieu and Fick Jr., eds., Marcel Dekker, New York, N.Y., Chapter 20, pp. 427-469; Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187: 9-18; Burton et al., 1994, *Advances in Immunology* 57:191-280; PCT Application No. PCT/GB91/01134; PCT Publications WO 90/02809, WO 91/10737, WO 92/01047, WO 92/18619, WO 93/11236, WO 95/15982, WO 95/20401, and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

As discussed herein, the CD30 binding agents include the amino acid sequence of a humanized heavy and/or light chain variable region. Antibodies can be humanized using a variety of techniques known in the art including, for example, CDR-grafting (see, e.g., EP 0 239 400; PCT publication WO 91/09967; U.S. Pat. Nos. 5,225,539; 5,530,101; and 5,585,089), veneering or resurfacing (see, e.g., EP 0 592 106; EP 0 519 596; Padlan, *Molecular Immunology*, 1991, 28(4/5):489-498; Studnicka et al., 1994, *Protein Engineering* 7(6):805-814; Roguska et al., 1994, *Proc. Natl. Acad. Sci. USA* 91:969-973), and chain shuffling (see, e.g., U.S. Pat. No. 5,565,332) (all of these references are incorporated by reference herein). Humanized antibodies and fragments thereof can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 0 012 023; Berter et al., 1988, *Science* 240:1041-43; Liu et al., 1987, *Proc. Natl. Acad. Sci. USA* 84:3439-43; Liu et al., 1987, *J. Immunol.* 139:3521-26; Sun et al., 1987, *Proc. Natl. Acad. Sci. USA* 84:214-18; Nishimura et al., 1987, *Cancer. Res.* 47:999-1005; Wood et al., 1985, *Nature* 314:446-449; Shaw et al., 1988, *J. Natl. Cancer Inst.* 80:1553-59; Morrison, 1985, *Science* 229:1202-07; Oi et al., 1986, *BioTechniques* 4:214; U.S. Pat. No. 5,225,539; Jones et al., 1986, *Nature* 321:552-25; Verhoeyan et al., 1988, *Science* 239:1534; and Beidler et al., 1988, *J Immunol.* 141:4053-60; each of which is incorporated herein by reference in its entirety.

Examples of techniques that can be used to produce single-chain antibodies include those described in U.S. Pat. Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, *Nature* 305:537-39). Because of the random assortment of immunoglobulin heavy and light chains, these hybridomas (quadromas) produce a potential mixture of different antibody molecules, of which one has the correct bispecific structure. Similar procedures are disclosed in International Publication No. WO 93/08829, and in Traunecker et al., 1991, *EMBO J.* 10:3655-59.

According to a different approach, antibody variable domains with the desired binding specificities (antibody-antigen combining sites) are fused to immunoglobulin constant domain sequences. The fusion typically is with an immunoglobulin heavy chain constant domain, comprising at least part of the hinge, $C_H2$, and $C_H3$ regions. In some embodiments, the fusion includes a first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an example of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (see, e.g., International Publication No. WO 94/04690, which is incorporated herein by reference in its entirety).

For further discussion of bispecific antibodies see, for example, Suresh et al., 1986, *Methods in Enzymology* 121: 210; Rodrigues et al., 1993, *J. Immunology* 151:6954-61; Carter et al., 1992, *Bio/Technology* 10:163-67; Carter et al., 1995, *J. Hematotherapy* 4:463-70; Merchant et al., 1998, *Nature Biotechnology* 16:677-81. Using such techniques, bispecific antibodies can be prepared for use in the treatment or prevention of disease as defined herein.

Bifunctional antibodies are also described in European Patent Publication No. 0 105 360. As disclosed in this reference, hybrid or bifunctional antibodies can be derived biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example in International Publication WO 83/03679 and European Patent Publication No. 0 217 577, both of which are incorporated herein by reference.

A CD30 binding agent can be a derivative of an anti-CD30 antibody. Generally, an anti-CD30 antibody derivative comprises an anti-CD30 antibody (e.g., an intact antibody, an antigen-binding fragment or conservatively substituted polypeptide) and at least one polypeptide region or other moiety heterologous to the anti-CD30 antibody. For example, an anti-CD30 antibody can be modified, e.g., by the covalent attachment of any type of molecule, such that the covalent attachment does not prevent the antibody derivative from specifically binding to CD30 via the antigen-binding region or region derived therefrom, or the effector region or portion thereof from specifically binding Fc receptor. Typical modifications include, e.g., glycosylation, deglycosylation, acetylation, pegylation, phosphorylation, amidation, derivatization by known protecting/blocking groups, proteolytic cleavage, linkage to a cellular ligand or other protein, and the like. Any of numerous chemical modifications may be carried out by known techniques, including, but not limited to specific chemical cleavage, acetylation, formylation, metabolic synthesis of tunicamycin, etc.

In some embodiments, the antibody derivative is a multimer, such as, for example, a dimer, comprising one or more monomers, where each monomer includes (i) an antigen-binding region of an anti-CD30 antibody, or a polypeptide region derived therefrom (such as, for example, by conservative substitution of one or more amino acids), and (ii) a multimerizing (e.g., dimerizing) polypeptide region, such that the antibody derivative forms multimers (e.g., homodimers) that specifically bind to CD30. In typical embodiments, an antigen binding region of an anti-CD30 antibody, or a polypeptide region derived therefrom, is recombinantly or chemically fused with a heterologous protein, wherein the heterologous protein comprises a dimerization or multimerization domain. Prior to administration of the antibody derivative to a subject for the purpose of treating or preventing immunological disorders or CD30-expressing cancers, the derivative is subjected to conditions that allow formation of a homodimer or heterodimer. A heterodimer, as used herein, may comprise identical dimerization domains but different CD30 antigen-binding regions, identical CD30 antigen-binding regions but different dimerization domains, or different CD30 antigen-binding regions and dimerization domains.

Typical dimerization domains are those that originate from transcription factors. In one embodiment, the dimerization domain is that of a basic region leucine zipper ("bZIP") (see, e.g., Vinson et al., 1989, *Science* 246:911-916). Useful leucine zipper domains include, for example, those of the yeast transcription factor GCN4, the mammalian transcription factor CCAAT/enhancer-binding protein C/EBP, and the nuclear transform in oncogene products, Fos and Jun. (See, e.g., Landschultz et al., 1988, *Science* 240:1759-64; Baxevanis and Vinson, 1993, *Curr. Op. Gen. Devel.* 3:278-285; O'Shea et al., 1989, *Science* 243:538-542.) In another embodiment, the dimerization domain is that of a basic region helix-loop-helix ("bHLH") protein. (See Murre et al., 1989, *Cell* 56:777-783. See also Davis et al., 1990, *Cell* 60:733-746; Voronova and Baltimore, 1990, *Proc. Natl. Acad. Sci. USA* 87:4722-26.) Particularly useful hHLH proteins are myc, max, and mac.

In yet other embodiments, the dimerization domain is an immunoglobulin constant region such as, for example, a heavy chain constant region or a domain thereof (e.g., a $C_H1$ domain, a $C_H2$ domain, and/or a $C_H3$ domain). (See, e.g., U.S. Pat. Nos. 5,155,027; 5,336,603; 5,359,046; and 5,349,053; EP 0 367 166; and WO 96/04388.)

Heterodimers are known to form between Fos and Jun (Bohmann et al., 1987, *Science* 238:1386-1392), among members of the ATF/CREB family (Hai et al., 1989, *Genes Dev.* 3:2083-2090), among members of the C/EBP family (Cao et al., 1991, *Genes Dev.* 5:1538-52; Williams et al., 1991, *Genes Dev.* 5:1553-67; Roman et al., 1990, *Genes Dev.* 4:1404-15), and between members of the ATF/CREB and Fos/Jun families (Hai and Curran, 1991, *Proc. Natl. Acad. Sci. USA* 88:3720-24). Therefore, when a CD30 binding agent is administered to a subject as a heterodimer comprising different dimerization domains, any combination of the foregoing may be used.

In other embodiments, an anti-CD30 antibody derivative is an anti-CD30 antibody conjugated to a second antibody (an "antibody heteroconjugate") (see, e.g., U.S. Pat. No. 4,676, 980). Heteroconjugates can be formed, for example, between an antibody that binds to CD30 (e.g., an antibody that has the CDRs and/or heavy chains of the monoclonal antibody AC10) and an antibody that binds to a surface receptor or receptor complex that mediates ADCC, phagocytosis, and/or CDC, such as CD16/FcγRIII, CD64/FcγRI, killer cell activating or inhibitory receptors, or the complement control protein CD59. In a typical embodiment, the binding of the portion of the multispecific antibody to the second cell surface molecule or receptor complex enhances the effector functions of an anti-CD30 antibody.

In some embodiments, the CD30 binding agent (e.g., anti-CD30 antibody or derivative thereof) competitively inhibits binding of mAbs AC10 or cAC10 to CD30, as determined by any method known in the art for determining competitive binding (such as e.g., the immunoassays described herein). In typical embodiments, the antibody competitively inhibits binding of AC10 to CD30 by at least 50%, at least 60%, at least 70%, or at least 75%. In other embodiments, the antibody competitively inhibits binding of mAbs AC10 or cAC10 to CD30 by at least 80%, at least 85%, at least 90%, or at least 95%.

The terms "specific binding" and "specifically binds" mean that the CD30 binding agent will react, in a highly selective manner, with its corresponding target, CD30 and not with the multitude of other antigens. Typically, the antibody binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen.

Antibodies and other binding agents can be assayed for specific binding to CD30 (e.g., human CD30) by any of various known methods. Immunoassays which can be used include, for example, competitive and non-competitive assay systems. Such assays are routine and well-known in the art. (See, e.g., Ausubel et al., eds., *Short Protocols in Molecular Biology* (John Wiley and Sons, Inc., New York, 4th ed. 1999); Harlow and Lane, *Using Antibodies: A Laboratory Manual* (Cold Spring Harbor Laboratory Press, Cold Spring Harbor, N.Y., 1999.))

Further, the binding affinity of a CD30 binding agent (e.g., anti-CD30 antibody or derivative thereof) to CD30 and the off-rate of a binding agent-CD30 interaction can be determined by competitive binding assays. One example of a competitive binding assay is a radioimmunoassay comprising the incubation of labeled CD30 (e.g., $^3$H or $^{125}$I) with the antibody of interest in the presence of increasing amounts of unlabeled CD30, and the detection of the antibody bound to the labeled CD30. The affinity of the antibody for CD30 and the binding off-rates can then be determined from the data by Scatchard plot analysis. Competition with a second antibody (such as e.g., mAb AC10) can also be determined using radioimmunoassays. In this case, CD30 is incubated with the antibody of interest conjugated to a labeled compound (e.g., $^3$H or $^{125}$I) in the presence of increasing amounts of an unlabeled second antibody. Alternatively, the binding affinity of an antibody to CD30 and the on- and off-rates of an antibody-CD30 interaction can be determined by surface plasmon resonance. In some embodiments, the anti-CD3 antibodies or derivatives thereof can be targeted to and accumulate on the membrane of a CD30-expressing cell.

CD30 binding agents (e.g., anti-CD30 antibody or derivative thereof) can be produced by methods known in the art for the synthesis of proteins, typically, e.g., by recombinant expression techniques. Recombinant expression of an antibody or derivative thereof typically involves construction of an expression vector containing a nucleic acid that encodes the binding agent. A vector for the production of the protein molecule may be produced by recombinant DNA technology using techniques known in the art. Standard techniques such as, for example, those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); *Short Protocols in Molecular Biology* (Ausubel et al, John Wiley and Sons, New York, 4th ed., 1999); and Glick and Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-CD30 antibody, an expression vector may encode a heavy or light chain thereof; or a heavy or light chain variable domain, operably linked to a promoter. An expression vector may include, for example, the nucleotide sequence encoding the constant region of the antibody molecule (see, e.g., PCT Publication WO 86/05807; PCT Publication WO 89/01036; and U.S. Pat. No. 5,122,464), and the variable domain of the antibody may be cloned into such a vector for expression of the entire heavy or light chain. The expression vector is transferred to a host cell by conventional techniques, and the transfected cells are then cultured by conventional techniques to produce the anti-CD30 antibody. In typical embodiments for the expression of double-chain antibodies, vectors encoding both the heavy and light chains can be co-expressed in the host cell for expression of the entire immunoglobulin molecule.

A variety of prokaryotic and eukaryotic host-expression vector systems can be utilized to express a CD30 binding agent (e.g., anti-CD30 antibody or derivative thereof). Typically, eukaryotic cells, particularly for whole recombinant anti-CD30 antibody molecules, are used for the expression of the recombinant protein. For example, mammalian cells such as Chinese hamster ovary cells (CHO; e.g., DG44), in conjunction with a vector such as the major intermediate early gene promoter element from human cytomegalovirus, is an effective expression system for the production of anti-CD30 antibodies and derivatives thereof (see, e.g., Foecking et al., 1986, *Gene* 45:101; Cockett et al., 1990, *Bio/Technology* 8:2).

CD30 binding aagents can also be expressed using the CHEF system. (See, e.g., U.S. Pat. No. 5,888,809.)

Other host-expression systems include, for example, plasmid-based expression systems in bacterial cells (see, e.g., Ruther et al., 1983, *EMBO* 1, 2:1791; Inouye and Inouye, 1985, *Nucleic Acids Res.* 13:3101-3109; Van Heeke and Schuster, 1989, *J. Biol. Chem.* 24:5503-5509); insect systems such as, e.g., the use of *Autographa californica* nuclear polyhedrosis virus (AcNPV) expression vector in *Spodoptera frugiperda* cells; and viral-based expression systems in mammalian cells, such as, e.g., adenoviral-based systems (see, e.g., Logan and Shenk, 1984, *Proc. Natl. Acad. Sci. USA* 81:355-359; Bittner et al., 1987, *Methods in Enzymol.* 153:51-544).

In addition, a host cell strain can be chosen that modulates the expression of the inserted sequences, or modifies and processes the gene product in the specific fashion desired. Appropriate cell lines or host systems can be chosen to ensure the correct modification and processing (e.g., glycosylation, phosphorylation, and cleavage) of the protein expressed. To this end, eukaryotic host cells which possess the cellular machinery for proper processing of the primary transcript and gene product can be used. Such mammalian host cells include, for example, CHO, VERO, BHK, HeLa, COS, MDCK, 293, 3T3, and W138.

A stable expression system is typically used for long-term, high-yield production of a recombinant CD30 binding agent. For example, cell lines that stably express the anti-CD30 antibody or derivative thereof can be engineered by transformation of host cells with DNA controlled by appropriate expression control elements (e.g., promoter, enhancer, sequences, transcription terminators, polyadenylation sites) and a selectable marker, followed by growth of the transformed cells in a selective media. The selectable marker confers resistance to the selection and allows cells to stably integrate the DNA into their chromosomes and grow to form foci which in turn can be cloned and expanded into cell lines. A number of selection systems can be used, including, for example, the herpes simplex virus thymidine kinase, hypoxanthineguanine phosphoribosyltransferase, and adenine phosphoribosyltransferase genes, which can be employed in tk$^-$, hgprt$^-$ or aprt$^-$ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin. Methods commonly known in the art of recombinant DNA technology can be routinely applied to select the desired recombinant clone, and such methods are described, for example, in Ausubel et al., eds., in the *Current Protocols in Molecular Biology* series of laboratory technique manuals, 1987-1999 Current Protocols,© 1994-1999 John Wiley and Sons, Inc.).; Kriegler, *Gene Transfer and Expression, A Laboratory Manual* (Stockton Press, N.Y., 1990); *Current Protocols in Human Genetics* (Dracopoli et al. eds., John Wiley and Sons, N.Y., 1994, Chapters 12 and 13); and Colberre-Garapin et al., 1981, *J. Mol. Biol.* 150:1.

The expression levels of an antibody or derivative can be increased by vector amplification. (See generally Bebbington and Hentschel, *The Use of Vectors Based on Gene Amplification for the Expression of Cloned Genes in Mammalian Cells in DNA Cloning*, Vol. 3 (Academic Press, New York, 1987).) When a marker in the vector system expressing an anti-CD30 antibody or derivative thereof is amplifiable, an increase in the level of inhibitor present in host cell culture media will select host cells that have increased copy number of a marker gene conferring resistance to the inhibitor. The copy number of an associated antibody gene will also be increased, thereby increasing expression of the antibody or derivative thereof (see, e.g., Crouse et al., 1983, Mol. Cell. Biol. 3:257).

Where a CD30 binding agent comprises both a heavy and a light chain (or derivatives thereof), the host cell may be co-transfected with two expression vectors, the first vector encoding the heavy chain protein and the second vector encoding the light chain protein. The two vectors may contain identical selectable markers which enable equal expression of heavy and light chain proteins. Alternatively, a single vector may be used which encodes, and is capable of expressing, both heavy and light chain proteins. In such situations, the light chain is typically placed before the heavy chain to avoid an excess of toxic free heavy chain (see, e.g., Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once a CD30 binding agent has been produced (e.g., by an animal, chemical synthesis, or recombinant expression), it can be purified by any suitable method for purification of proteins, including, for example, by chromatography (e.g., ion exchange or affinity chromatography (such as, for example, Protein A chromatography for purification of antibodies having an intact Fc region)), centrifugation, differential solubility, or by any other standard technique for the purification of proteins. An anti-CD30 antibody or derivative thereof can, for example, be fused to a marker sequence, such as a peptide, to facilitate purification by affinity chromatography. Suitable marker amino acid sequences include, e.g., a hexa-histidine peptide, such as the tag provided in a pQE vector (QIAGEN, Inc., Chatsworth, Calif., 91311), and the "HA" tag, which corresponds to an epitope derived from the influenza hemagglutinin protein (Wilson et al., 1984, Cell 37:767), and the "flag" tag.

The ability of a CD30 binding agent to exert a cytostatic or cytotoxic effect on CD30-expressing cancer cells or an immunomodulatory effect on a CD30-expressing immune cell can be determined by the methods described infra or as known in the art.

Typically, the CD30 binding agent is substantially purified (e.g., substantially free from substances that limit its effect or produce undesired side-effects). In some embodiments, the CD30 binding agent is at least about 40% pure, at least about 50% pure, or at least about 60% pure. In some embodiments, the CD30 binding agent is at least about 60-65%, 65-70%, 70-75%, 75-80%, 80-85%, 85-90%, 90-95%, or 95-98% pure. In some embodiments, the CD30 binding agent is approximately 99% pure.

III. Other CD30 Binding Agents

Further CD30 binding agents include fusion proteins (i.e., proteins that are recombinantly fused or chemically conjugated, including both covalent and non-covalent conjugation) to heterologous proteins (of typically at least 10, 20, 30, 40, 50, 60, 70, 80, 90 or at least 100 amino acids). In some embodiments, such a CD30 binding agent includes the amino acid sequence of a humanized heavy and/or light chain variable region that specifically binds to CD30 and an immunoglobulin effector region or a functional equivalent thereof. As used herein, a functional equivalent of an immunoglobulin effector region binds to an Fc receptor on an immune cell with phagocytic or lytic activity, or the immunoglobulin effector region binds to one or more components of the complement system. The linkage of the CD30 binding portion to the heterologous protein is not necessarily direct, but may occur through a linker sequence(s).

For example, a CD30 binding agent can be produced recombinantly by fusing the coding region of one or more of the CDRs of mAb AC10, or a humanized AC10 variable region in frame with a sequence coding for a heterologous protein. The heterologous protein optionally can include an effector region or a functional equivalent thereof and may provide one or more of the following characteristics: promote stable expression; provide a means of facilitating high yield recombinant expression; and/or provide a multimerization domain.

In some embodiments, the CD30 binding agent can deplete or inhibit the proliferation of CD30-expressing cells alone, without conjugation to a cytotoxic agent. In some embodiments, the CD30 binding agent is conjugated to a therapeutic agent.

In an aspect, a CD30 binding agent can include CD153 and variants or fragments thereof that bind to CD30 (e.g., human CD153 that binds to human CD30) or peptides, ligands and other molecules that specifically bind to CD30. In one aspect, the CD30 binding agent does not include CD153 and variants or fragments thereof that bind to CD30.

A CD30 binding agent can be identified using any method suitable for screening for protein-protein interactions. Typically, proteins are initially identified by their ability to specifically bind to CD30. The ability of such a binding protein to exert a cytostatic or cytotoxic effect can be determined. Among the traditional methods which can be employed are "interaction cloning" techniques which entail probing expression libraries with labeled CD30 in a manner similar to the technique of antibody probing of λgt11 libraries. By way of example and not limitation, this can be achieved as follows: a cDNA clone encoding CD30 can be modified at the C-terminus by inserting the phosphorylation site for the heart muscle kinase (HMK) (see, e.g., Blanar and Rutter, 1992, *Science* 256:1014-18). The recombinant protein is expressed in *E. coli* and purified on a GDP-affinity column to homogeneity (Edery et cal., 1988, *Gene* 74:517-25) and labeled using $\gamma^{32}$P-ATP and bovine heart muscle kinase (Sigma-Aldrich Co., St. Louis, Mo.) to a specific activity of $1\times10^8$ cpm/μg, and used to screen a human placenta λgt11 cDNA library in a "far-Western assay" (Blanar and Rutter, 1992, *Science* 256: 1014-18). Plaques that interact with the CD30 probe are isolated. The cDNA inserts of positive λ plaques are released and subcloned into a vector suitable for sequencing, such as pBluescript KS (Stratagene, La Jolla, Calif.).

One method which detects protein interactions in vivo is the two-hybrid system. One version of this system has been described (Chien et al., 1991, *Proc. Natl. Acad. Sci. USA* 88:9578-82) and is commercially available from Clontech (Palo Alto, Calif.).

Once a CD30-binding protein is identified, its ability (alone or when multimerized or fused to a dimerization or multimerization domain) to exert a cytostatic or cytotoxic effect on CD30-expressing cancer cells or an immunomodulatory effect on a CD30-expressing immune cell can be determined by the methods described infra.

IV. Assays for Cytotoxic, Cytostatic, and Immunomodulatory Activities

Methods of determining whether a CD30 binding agent mediates a cytotoxic, cytostatic, and/or immunomodulatory activity against a target cell are known. Illustrative examples of such methods are described infra.

For determining whether a CD30 binding agent mediates antibody-dependent cellular cytotoxicity against activated immune cells or CD30-expressing cancer cells, an assay that measures target cell death in the presence of antibody and effector immune cells may be used. An assay used to measure this type of cytotoxicity can be based on determination of $^{51}$Cr release from metabolically-labeled targets cells after incubation in the presence of effector cells and target-specific antibody (see, e.g., Perussia and Loza, 2000, *Methods in Molecular Biology* 121:179-92 and "$^{51}$Cr Release Assay of Antibody-Dependent Cell-Mediated Cytotoxicity (ADCC)," in *Current Potocols in Immunology*, Coligan et al. eds., Wileyand Sons, 1993). For example, activated immune cells (e.g., activated lymphocytes) or CD30-expressing cancer cells labeled with Na$_2$$^{51}$CrO$_4$ and plated at a density of 5,000 cells per well of a 96-well plate can be treated with varying concentrations of anti-CD30 antibody for 30 minutes then mixed with normal human peripheral blood mononuclear cells (PBMC) for 4 hours. The membrane disruption that accompanies target cell death releases $^{51}$Cr into the culture supernatant which may be collected and assessed for radioactivity as a measure of cytotoxic activity. Other assays to measure ADCC may involve nonradioactive labels or be based on induced release of specific enzymes. For example, a non-radioactive assay based on time-resolved fluorometry is commercially available (Delphia, Perkin Elmer). This assay is based on loading target cells with an acetoxymethyl ester of fluorescence enhancing ligand (BATDA) that penetrates the cell membrane then hydrolyses to form a membrane impermeable hydrophilic ligand (TDA). When mixed with target specific antibody and PBMC effector cells, TDA is released from lysed cells and is available to form a highly fluorescent chelate when mixed with Europium. The signal, measured with a time-resolved fluorometer, correlates with the amount of cell lysis.

To determine whether a CD30 binding agent mediates antibody-dependent cellular phagocytosis against activated immune cells or CD30-expressing cancer cells, an assay that measures target cell internalization by effector immune cells (e.g., fresh cultured macrophages or established macrophage-like cell line) may be used (see, e.g., Munn and Cheung, 1990, *J. Exp. Med.* 172:231-37; Keler et al., 2000, *J. Immunol.* 164:5746-52; Akewanlop et al., 2001, *Cancer Res.* 61:4061-65). For example, target cells may be labeled with a lipophilic membrane dye such as PKH167 (Sigma-Aldrich Co.), coated with target-specific antibody, and mixed with effector immune cells for 4-24 hours. The effector cells may then be identified by counterstaining with a fluorochrome-labeled antibody specific for a phagocytic cell surface marker (e.g., CD14) and the cells analyzed by two-color flow cytometry or fluoresence microscopy. Dual-positive cells represent effector cells that have internalized target cells. For these assays, effector cells may be monocytes derived from PBMC that have been differentiated into macrophages by culture for 5-10 days with M-CSF or GM-CSF (see, e.g., Munn and Cheung, supra). Human macrophage-like cell lines U937 (Larrick et al., 1980, *J. Immunology* 125:6-12) or THP-1 (Tsuchiya et al., 1980, *Int. J. Cancer* 26:171-76) which are available from ATCC may be used as an alternative phagocytic cell source.

Methods of determining whether an antibody mediates complement-dependent cytotoxicity upon binding to target cells are also known. The same methods can be applied to determine whether a CD30 binding agent mediates CDC activated immune cells or CD30-expressing cancer cells. Illustrative examples of such methods are described infra.

The source of active complement components can either be normal human serum or purified from laboratory animal including rabbits. In a standard assay, a CD30 binding agent is incubated with CD30-expressing activated immune cells (e.g., activated lymphocytes) or CD30-expressing cancer cells in the presence of complement. The ability of such CD30 binding agent to mediate cell lysis can be determined by several readouts. In one example, a Na$^{51}$CrO$_4$ release assay is used. In this assay, target cells are labeled with Na$^{51}$CrO$_4$. Unincorporated Na$^{51}$CrO$_4$ is washed off and cells are plated at a suitable density, typically between 5,000 to 50,000 cells/well, in a 96-well plate. Incubation with the CD30 binding agent in the presence of normal serum or purified complement components is typically for 2-6 hours at 37° C. in a 5% CO$_2$ atmosphere.

Released radioactivity, indicating cell lysis, is determined in an aliquot of the culture supernatant by gamma ray counting. Maximum cell lysis is determined by releasing incorporated Na$^{51}$CrO$_4$ by detergent (0.5-1% NP-40 or Triton X-100) treatment. Spontaneous background cell lysis is determined in wells where only complement is present in the absence of CD30 binding agents. Percentage cell lysis is calculated as (CD30 binding agent-induced lysis—spontaneous lysis)/maximum cell lysis. The second readout is a reduction of metabolic dyes, e.g., Alamar Blue, by viable cells. In this assay, target cells are incubated with CD30 binding agent with complement and incubated as described above. At the end of incubation, 1/10 volume of Alamar Blue (Biosource International, Camarillo, Calif.) is added. Incubation is continued for up to 16 hours at 37° C. in a 5% CO$_2$ atmosphere. Reduction of Alamar Blue as an indication of metabolically active viable cells is determined by fluorometric analysis with excitation at 530 nm and emission at 590 nm. The third readout is cellular membrane permeability to propidium iodide (PI). Formation of pores in the plasma membrane as a result of complement activation facilitates entry of PI into cells where it will diffuse into the nuclei and bind DNA. Upon binding to DNA, PI fluorescence at 600 nm significantly increases. Treatment of target cells with a CD30 binding agent and complement is carried out as described above. At end of incubation, PI is added to a final concentration of 5 µg/ml. The cell suspension is then examined by flow cytometry using a 488 nm argon laser for excitation. Lysed cells are detected by fluorescence emission at 600 nm.

Methods of evaluating an antibody for growth inhibition effects on a target cell are known in the art. In a non-limiting example, the antibody, at 10 µg/ml in 50 mM Tris-HCl (pH8.5), is first immobilized onto plastic 96-well tissue culture plates by overnight incubation at 4° C., followed by two washes with PBS to remove unbound antibody. Cells are then added in 100 µl of complete medium at a concentration of 5000 cells/well. After a 48 hr incubation at 37° C., 5% CO$_2$, the cells are labeled with [$^3$H]thymidine by the addition of 50 µl of complete medium containing 0.5 µCi of [$^3$H]thymidine for two hr. The labeled cells are precipitated onto a filter, and the bound [$^3$H]thymidine is quantitated by liquid scintillation counting. Measurement of the level of DNA synthesis is relative to cells in untreated control wells. Other methods for evaluating the cytotoxic and/or cytostatic properties of a CD30 binding agent are disclosed in, for example, U.S. Published Application Nos. 2005-0123536 and 2004-0018194 and International Patent Publication WO 02/43661 (the disclosures of which are incorporated by reference herein).

Methods of determining whether an antibody drug conjugate mediates cytotoxicity or cytostatic effects on target cells are also known. The same methods (supra) can be applied to determine whether a CD30 binding agent mediates cytotoxicity or cytostatic effects on activated immune cells or CD30-expressing cancer cells in the absence of effector cells.

V. Animal Models of Immunological Disorders or CD30 Expressing Cancers

The CD30 binding agents can be tested or validated in animal models of immunological disorders or CD30-expressing cancers. A number of established animal models of immunological disorders or CD30-expressing cancers are known to the skilled artisan, any of which can be used to assay the efficacy of the anti-CD30 antibody or derivative. Non-limiting examples of such models are described infra.

Examples of animal models of systemic and organ-specific autoimmune diseases, including diabetes, systemic lupus erythematosus, systemic sclerosis, Sjögren's Syndrome, experimental autoimmune encephalomyelitis (multiple sclerosis), thyroiditis, myasthenia gravis, arthritis, uveitis, and inflammatory bowel disease, have been described by Bigazzi, "Animal Models of Autoimmunity: Spontaneous and Induced," in *The Autoimmune Diseases* (Rose and Mackay eds., Academic Press, 1998) and in "Animal Models for Autoimmune and Inflammatory Disease," in *Current Protocols in Immunology* (Coligan et al. eds., Wiley and Sons, 1997).

Allergic conditions, e.g., asthma and dermatitis, can also be modeled in rodents. Airway hypersensitivity can be induced in mice by ovalbumin (Tomkinson et al., 2001, *J. Immunol.* 166:5792-800) or *Schistosoma mansoni* egg antigen (Tesciuba et al., 2001, *J. Immunol.* 167:1996-2003). The Nc/Nga strain of mice show marked increase in serum IgE and spontaneously develop atopic dermatitis-like leisons (Vestergaard et al., 2000, *Mol. Med. Today* 6:209-10; Watanabe et al., 1997, *Int. Immunol.* 9:461-66; Saskawa et al., 2001, *Int. Arch. Allergy Immunol.* 126:239-47).

Injection of immunocompetent donor lymphocytes into a lethally irradiated histo-incompatible host is a classical approach to induce GVHD (graft versus host disease) in B6D2F1 mice. Alternatively, the parent B6D2F1 murine model provides a system to induce both acute and chronic GVHD. In this model the B6D2F1 mice are F1 progeny from a cross between the parental strains of C57BL/6 and DBA/2 mice. Transfer of DBA/2 lymphoid cells into non-irradiated B6D2F1 mice causes chronic GVHD, whereas transfer of C57BL/6, C57BL/10 or B10.D2 lymphoid cells causes acute GVHD (Slayback et al., 2000, *Bone Marrow Transpl.* 26:931-938; Kataoka et al., 2001, *Immunology* 103:310-318).

Additionally, both human hematopoietic stem cells and mature peripheral blood lymphoid cells can be engrafted into SCID mice, and these human lympho-hematopoietic cells remain functional in the SCID mice (McCune et al., 1988, *Science* 241:1632-1639; Kamel-Reid and Dick, 1988, *Science* 242:1706-1709; Mosier et al., 1988, *Nature* 335:256-259). This has provided a small animal model system for the direct testing of potential therapeutic agents on human lymphoid cells. (See, e.g., Tournoy et al., 2001, *J. Immunol.* 166:6982-6991.)

Moreover, small animal models to examine the in vivo efficacies of the anti-CD30 antibodies or derivatives can be created by implanting CD30-expressing human tumor cell lines into appropriate immunodeficient rodent strains, e.g., athymic nude mice or SCID mice. Examples of CD30-expressing Hodgkin's lymphoma lines are L428 (see, e.g., Wahl et al., 2002, *Cancer Res.* 62:3736-42), L540 (e.g., Wahl et al., 2002, *Cancer Res.* 62:3736-42) and L540cy (Barth et al., 2000, *Blood* 95:3909-14; Wahl et al., 2002, *Cancer Res.* 62:3736-42). Other examples of CD30-expressing Hodgkin's lymphoma lines are KMH2, HDLM-2, L1236, Hs445, and RPMI-6666. Examples of CD30-expressing anaplastic large cell lymphoma cell lines are Karpas 299 and SU-DHL-1. (See, e.g., Nagata et al., 2005, *Proc. Natl. Acad. Sci. USA* 102:7946-51; Wahl et al., 2002, *Cancer Res.* 62:3736-42). Other examples of CD30-expressing anaplastic large cell lymphoma cell lines are DEL, SR786, and SUP-M2. Examples of Adult T-cell Leukemia (ATL) cell lines include ATL-derived T-cell lines (e.g., TL-OmI, KOB, KK1 and ST1), HTLV-1 transformed cell lines (e.g., HUT-102, C5/MJ, MT-4 and SLB-1) and HTLV-1 negative T-cell lines (e.g., Jurkat and MOLT-4). (See,e.g., Higuchi et al., 2005, *Retrovirology* 2:29.) An example of a CD30-expressing embryonal carcinoma cell line is Tera-2. An example of a CD30-expressing erythroleukemia cell line is K562 AZQR. Examples of CD30-expressing multiple myeloma cell lines are AMO-1 and L363. Examples of CD30-expressing cutaneous T cell lymphoma cell lines are HH and HUT-78.

These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-CD30 antibody or derivatives as described herein on modulating in vivo tumor growth.

VI. CD30 Associated Disorders

The CD30 binding agents described herein are useful for treating or preventing a CD30-expressing cancer or an immunological disorder characterized by expression or overexpression of CD30. Such expression of CD30 can be due to, for example, increased CD30 protein levels on the cell surface and/or altered antigenicity of the expressed CD30. Treatment or prevention of the immunological disorder, according to the methods described herein, is achieved by administering to a subject in need of such treatment or prevention an effective amount of the CD30 binding agent, whereby the agent (i) binds to activated immune cells that express CD30 and that are associated with the disease state and (ii) exerts a cytotoxic, cytostatic, or immunomodulatory effect on the activated immune cells.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., *Fundamental Immunology*, William E. Paul ed., Raven Press, N.Y., 3rd ed. 1993.)

Specific examples of such immunological diseases include, but are not limited to, rheumatoid arthritis, multiple sclerosis, endocrine opthalmopathy, uveoretinitis, systemic lupus erythematosus, myasthenia gravis, Grave's disease, glomerulonephritis, autoimmune hepatological disorder, autoimmune inflammatory bowel disease, anaphylaxis, allergic reaction, Sjogren's syndrome, juvenile onset (Type I) diabetes mellitus, primary biliary cirrhosis, Wegener's granulomatosis, fibromyalgia, inflammatory bowel disease, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), adult onset diabetes mellitus (Type II diabetes), male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic encephalomyelitis, toxic epidermal necrolysis, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Eaton-Lambert syndrome, relapsing polychondritis, cryoglobulinemia, Waldenstrom's macroglobulemia, Epstein-Barr virus infection, mumps, Evan's syndrome, and autoimmune gonadal failure.

Accordingly, the methods described herein encompass treatment of disorders of B lymphocytes (e.g., systemic lupus erythematosus, Goodpasture's syndrome, rheumatoid arthritis, and type I diabetes), $Th_1$ lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or graft versus host disease), or $Th_2$-lymphocytes (e.g., atopic dermatitis, systemic lupus erythematosus, atopic asthma, rhinoconjunctivitis, allergic rhinitis, or chronic graft versus host disease). Generally, disorders involving dendritic cells involve disorders of $Th_1$-lymphocytes or $Th_2$-lymphocytes.

The anti-CD30 antibodies and derivatives as described herein are also useful for treating or preventing a CD30-expressing cancer. Treatment or prevention of a CD30-expressing cancer, according to the methods described herein, is achieved by administering to a subject in need of such treatment or prevention an effective amount of the anti-CD30 antibody or derivative, whereby the antibody or derivative (i) binds to CD30-expressing cancer cells and (ii) exerts a cytotoxic or cytostatic effect to deplete or inhibit the proliferation of the CD30-expressing cancer cells.

CD30-expressing cancers that can be treated or prevented by the methods described herein include, for example, Hodgkin's Disease, anaplastic large cell lymphoma (ALCL) (e.g., cutanoeous or systemic), transformed mycosis fungoides, lymphatoid papulosis, adult T-cell lymphoma. (ATL), angioimmunoblastic lymphadenopathy (AILD)-like T cell lymphoma, HIV associated body cavity based lymphomas, embryonal carcinomas, undifferentiated carcinomas of the rhino-pharynx (e.g., Schmincke's tumor), Castleman's disease, Kaposi's Sarcoma, T cell lymphoid neoplasia caused by HTLV infection (e.g., adult T-cell leukemia/lymphoma), and other T-cell or B-cell lymphomas.

VII. Pharmaceutical Compositions Comprising CD30 Binding Agents and Administration Thereof A composition comprising a CD30 binding agent (e.g., an anti-CD30 antibody or derivative) can be administered to a subject having or at risk of having an immunological disorder or a CD30-expressing cancer. The invention further provides for the use of a CD30 binding agent (e.g., an anti-CD30 antibody or derivative) in the manufacture of a medicament for prevention or treatment of a CD30 expressing cancer or immunological disorder. The term "subject" as used herein means any mammalian patient to which a CD30 binding agent can be administered, including, e.g., humans and non-human mammals, such as primates, rodents, and dogs. Subjects specifically intended for treatment using the methods described herein include humans. The antibodies or derivatives can be administered either alone or in combination with other compositions in the prevention or treatment of the immunological disorder or CD30-expressing cancer.

Various delivery systems are known and can be used to administer the CD30 binding agent. Methods of introduction include but are not limited to intradermal, intramuscular, intraperitoneal, intravenous, subcutaneous, intranasal, epidural, and oral routes. The CD30 binding agent can be administered, for example by infusion or bolus injection, by absorption through epithelial or mucocutaneous linings (e.g., oral mucosa, rectal and intestinal mucosa, and the like) and can be administered together with other biologically active agents such as therapeutic agents. Administration can be systemic or local. In some embodiments, a CD30 binding agent is administered by intravenous infusion, by subcutaneous infusion, as an intravenous bolus, or as a subcutaneous bolus.

In specific embodiments, the CD30 binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the CD30 binding agent (e.g., anti-CD30 antibody or derivative) does not absorb are used.

In other embodiments, the CD30 binding agent (e.g., anti-CD30 antibody or derivative) is delivered in a controlled release system. In one embodiment, a pump may be used. (See, e.g., Langer, 1990, *Science* 249:1527-1533; Sefton, 1989, *CRC Crit. Ref. Biomed. Eng.* 14:201; Buchwald et al., 1980, *Surgery* 88:507; Saudek et al., 1989, *NEngl. J. Med.* 321:574.) In another embodiment, polymeric materials can be used. (See, e.g., *Medical Applications of Controlled Release*, Langer and Wise eds., CRC Press, Boca Raton, Fla., 1974; *Controlled Drug Bioavailability, Drug Product Design and Performance*, Smolen and Ball eds., Wiley, New York, 1984; Ranger and Peppas, 1983, *Macromol. Sci. Rev. Macromol. Chem.* 23:61. See also Levy et al., 1985, *Science* 228:190; During et al., 1989, *Ann. Neural.* 25:351; Howard et al., 1989, *J. Neurosurg.* 71:105.) Other controlled release systems are discussed, for example, in Langer, supra.

A CD30 binding agent (e.g., an anti-CD30 antibody or derivative) can be administered as pharmaceutical compositions comprising a therapeutically effective amount of the binding agent and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Other suitable pharmaceutical excipients include, for example, amino acids (e.g., glycine, arginine, histidine), detergents (e.g., nonionic detergents), sugar alcohols (e.g., mannitol, sorbitol), polyols, and the like. The composition, if desired, can also contain minor amounts of wetting or emulsifying agents, or pH buffering agents (e.g., amino acids, citate, phosphate). These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "*Remington: The Science and Practice of Pharmacy*, (formerly *Remington's Pharmaceutical Sciences*), Mack Publishing Co. Such compositions will contain a therapeutically effective amount of the CD30 binding agent, typically in purified form, together with a suitable amount of carrier so as to provide the form for proper administration to the subject. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a CD30 binding agent (e.g., an anti-CD30 antibody or derivative) in lyophilized form and (b) a second container containing a pharmaceutically acceptable diluent (e.g., sterile water) for injection. The pharmaceutically acceptable diluent can be used for reconstitution or dilution of the lyophilized anti-CD30 antibody or derivative. Optionally associated with such container(s) can be a notice in the faint prescribed by a governmental agency regulating the manufacture, use or sale ofphaiin.aceuticals or biological products, which notice reflects approval by the agency of manufacture, use or sale for human administration.

The amount of the CD30 binding agent (e.g., anti-CD30 antibody or derivative) that is effective in the treatment or prevention of an immunological disorder or CD30-expressing cancer can be determined by standard clinical techniques. In addition, in vitro assays may optionally be employed to help identify optimal dosage ranges. The precise dose to be employed in the formulation will also depend on the route of administration, and the stage of immunological disorder or CD30-expressing cancer, and should be decided according to the judgment of the practitioner and each subject's circumstances. Effective doses may be extrapolated from dose-response curves derived from in vitro or animal model test systems.

For example, toxicity and therapeutic efficacy of the anti-CD30 antibody or derivative can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A CD30 binding agent (e.g., an anti-CD30 antibody or derivative) that exhibits a large therapeutic index is preferred. Where a CD30 binding agent exhibits toxic side effects, a delivery system that targets the CD30 binding agent to the site of affected tissue can be used to minimize potential damage non-CD30-expressing cells and, thereby, reduce side effects.

The data obtained from the cell culture assays and animal studies can be used in formulating a range of dosage for use in humans. The dosage of the CD30 binding agent typically lies within a range of circulating concentrations that include the $ED_{50}$ with little or no toxicity. The dosage may vary within this range depending upon the dosage form employed and the route of administration utilized. For any CD30 binding agent used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Generally, the dosage of an anti-CD30 antibody or derivative administered to a subject with an immunological disorder or CD30-expressing cancer is typically 0.1 mg/kg to 100 mg/kg of the subject's body weight. The dosage administered to a subject is 0.1 mg/kg to 50 mg/kg, 0.1 mg/kg to 10 mg/kg, 1 mg/kg to 30 mg/kg, 1 mg/kg to 20 mg/kg, 1 mg/kg to 15 mg/kg, or 1 mg/kg to 10 mg/kg of the subject's body weight.

In some embodiments, the pharmaceutical compositions comprising the CD30 binding agent can further comprise a therapeutic agent (i.e., a cytotoxic or immunomodulatory agent such as, for example, any of those described herein). The CD30 binding agent can be co-administered in combination with one or more therapeutic agents for the treatment or prevention of immunological disorders or CD30-expressing cancers. For example, combination therapy can include a cytostatic, cytotoxic, or immunomodulatory agent (for example, a cytostatic, cytotoxic, or immunomodulatory agent such as those conventionally used for the treatment of cancers or immunological disorders). Combination therapy can also include, e.g., administration of an agent that targets a receptor or receptor complex other than CD30 on the surface of activated lymphocytes, dendritic cells or CD30-expressing cancer cells. An example of such an agent includes a second, non-CD30 antibody that binds to a molecule at the surface of an activated lymphocyte, dendritic cell or CD30-expressing cancer cell. Another example includes a ligand that targets such a receptor or receptor complex. Typically, such an antibody or ligand binds to a cell surface receptor on activated lymphocytes, dendritic cell or CD30-expressing cancer cell and enhances the cytotoxic or cytostatic effect of the anti-CD30 antibody by delivering a cytostatic or cytotoxic signal to the activated lymphocyte, dendritic cell or CD30-expressing cancer cell.

Such combinatorial administration can have an additive or synergistic effect on disease parameters (e.g., severity of a symptom, the number of symptoms, or frequency of relapse).

With respect to therapeutic regimens for combinatorial administration, in a specific embodiment, a CD30 binding agent is administered concurrently with a therapeutic agent. In another specific embodiment, the therapeutic agent is administered prior or subsequent to administration of the CD30 binding agent, by at least an hour and up to several months, for example at least an hour, five hours, 12 hours, a day, a week, a month, or three months, prior or subsequent to administration of the CD30 binding agent.

Useful classes of cytotoxic or immunomodulatory agents include, for example, antitubulin agents, auristatins, DNA minor groove binders, DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins and derivatives thereof (e.g., auristatin E, AEB, AEVB, AFP, MMAE, MMAF), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to the anti-CD30 antibodies or derivatives thereof.

In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. (See, e.g., U.S. Published Application Nos. 2004-0157782 A1 and 2005-0238649; the disclosures of which are incorporated by reference herein.)

In specific embodiments, the cytotoxic agent is a DNA minor groove binding agent. (See, e.g., U.S. Pat. No. 6,130,237.) For example, in some embodiments, the minor groove binding agent is a CBI compound. In other embodiments, the minor groove binding agent is an enediyne (e.g., calicheamicin).

Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In some embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, *Cancer Res.* 52:127-131).

In some embodiments, the therapeutic agent is not a radioisotope.

In some embodiments, the cytotoxic or immunomodulatory agent is an antimetabolite. The antimetabolite can be, for example, a purine antagonist (e.g. azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the cytotoxic or immunomodulatory agent is tacrolimus, cyclosporine or rapamycin. In further embodiments, the cytoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine and zoledronate.

In some embodiments, the therapy is a combined therapy, such as CHOP (cyclophosphamide, doxorubicin, vincristine, prednisolone), R-CHOP (rituximab, cyclophosphamide, doxorubicin, vincristine, prednisolone), ACVBP (doxorubicin, cyclophosphamide, vindesine, bleomycin, prednisone), CNOP (cyclophosphamide, mitoxantrone, vincristine, prednisone), m-BACOD (methotrexate, bleomycin, doxorubicin, cyclophosphamide, vincristine, dexamethasone, leucovorin), MACOP-B (methotrexate, doxorubicin, cyclophosphamide, vincristine, prednisone, bleomycin, leucovorin), ProMACE CytaBOM (prednisone, doxorubicin, cyclophosphamide, etoposide, cytarabine, bleomycin, vincristine, methotrexate, leucovorin) or GVD (gemcitabine, vincristine, doxorubicin).

In additional embodiments, the CD30 binding agent is administered with an antibody; e.g., HERCEPTIN® (trastuzumab, a humanized murine anti-HER2 monoclonal antibody; Genentech, Inc., South San Francisco, Calif.); RITUXAN® (rituximab, a human/mouse chimeric anti-CD20 monoclonal antibody; Genentech, Inc., South San Francisco, Calif.); OVAREX® (oregovomab, a murine anti-CA125 monoclonal antibody; AltaRex Corporation, Waltham, Mass.); PANOREX® (edrocolomab, a murine anti-17-1A monoclonal antibody; GlaxoSmithKline, Middlesex, UK); Erbitux® (cetuximab, a human/mouse chimeric anti-EGFR monoclonal antibody; Imclone Systems Inc., New York, N.Y.); Vitaxin® (MEDI-522, a humanized murine anti-integrin monoclonal antibody; MedImmune, Inc., Gaithersburg, Md.); Campath® (alemtuzumab, a humanized murine anti-CD52 monoclonal antibody; Millennium Pharmaceuticals, Inc., Cambridge, Mass.); Smart MI95 (a humanized murine anti-CD33 monoclonal antibody; Protein Design Labs, Inc., Fremont, Calif.); LymphoCide (epratuzumab, a humanized murine anti-CD22 monoclonal antibody; Immunomedics, Inc., Morris Plains, N.J.); Smart ID 10 (a humanized murine anti-HLA-DR monoclonal antibody; Protein Design Labs, Inc., Fremont, Calif.); Oncolym (a radiolabeled murine anti-HLA-Dr10 monoclonal antibody; Techniclone, Inc., Tustin, Calif.); Allomune (a humanized murine anti-CD2 monoclonal antibody; BioTransplant, CA;); Avastin (a humanized murine anti-VEGF monoclonal antibody; Genentech, Inc., South San Francisco, Calif.); or CEAcide (a humanized murine anti-CEA monoclonal antibody; Immunomedics, Morris Plains, N.J.).

Other suitable antibodies include, but are not limited to, antibodies against the following antigens: CA125, CA15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti transferrin receptor, p97, MUC1-KLH, CEA, gp100, MART1, Prostate Specific Antigen, IL-2 receptor, CD20, CD52, CD33, CD22, human chorionic gonadotropin, CD38, CD30, mucin, P21, MPG, and Neu oncogene product.

In some embodiments, the therapeutic agent is an immunomodulatory agent. The immunomodulatory agent can be, for example, gancyclovir, etanercept, tacrolimus, cyclosporine, rapamycin, cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some typical embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SKand F-104493, Leo Denmark SR-2566, Tanabe T-757 and Teijin TEI-1338.

VIII. Immunoconjugates

The invention also pertains to immunoconjugates comprising a CD30 binding agent, in one aspect an antibody, conjugated to a therapeutic agent such as a chemotherapeutic agent, a growth inhibitory agent, a cytotoxin (e.g., an enzymatically active toxin of bacterial, fungal, plant, or animal origin, or fragments thereof), immunomodulators, chelators, boron compounds, photoactive agents, photoactive dyes, or a radioactive isotope (i.e., a radioconjugate). Such immunoconjugates are also referred herein as "antibody drug conjugates".

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

In specific embodiments, the cytotoxic or cytostatic agent is auristatin E (also known as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis, structure, and conjugation of auristatin E and its derivatives are described in U.S. Pat. No. 6,884,869; U.S. Published Application Nos. 2004-0157782 A1 and 2005-0238649; International Patent Application No. PCT/US03/24209, International Patent Application No. PCT/US02/13435, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414 (the disclosures of which are incorporated by reference herein). The synthesis, structure, and conjugation of MMAF and its derivatives are described in International Patent Application No. PCT/US04/038392, incorporated herein by reference in its entirety.

Methods for carrying out the conjugation of therapeutic agents to an antibody are described in, for example, U.S. Published Application Nos. 2004-0157782 A1 and 2005-0238649 and International Patent Application No, PCT/US04/038392.

EXAMPLES

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ). Cell culture reagents were obtained from Invitrogen Corp., Carlsbad, Calif.

Example 1

Production of Humanized Anti-CD30 Antibody Variants

To humanize cAC10, human acceptor sequences were chosen from human germline exon $V_H$, $J_H$, Vκ and Jκ sequences. Germline acceptor sequences were selected by comparison of the cAC10 heavy chain and light chain variable region amino acid sequences (SED ID NO:2 and 24, respectively), using the BLAST program. Based on this sequence comparison, germline $V_H$ exon $V_H$1-2 and $J_H$ exon $J_H$-4 were chosen as acceptor sequences for cAC10 $V_H$ domain humanization (SEQ ID NO:45). Germline Vκ exon B3 and Jκ exon Jκ-1 were chosen as acceptor sequences for cAC10 $V_L$ domain humanization (SEQ ID NO:46).

AC10 murine CDRs, determined according to the Kabat definition (Kabat et al., Sequences of Proteins of Immunological Interest, Fifth Edition (1991)), were grafted onto the selected human germline sequences. Briefly, in the procedure used synthetic overlapping oligonucleotides spanning the human $V_H$ or $V_L$ domain, including the CDRs were generated and each domain was assembled by PCR overlap extension. Restriction sites incorporated into the PCR product were used to directionally clone the $V_H$ and $V_L$ domains into a pCMV expression vector in frame with a sequence encoding human IgG$_1$ constant domain or Kappa constant domain, respectively. The resulting plasmids were designated pAC10hVHd and pAC10hVLa, respectively.

DNA sequence analysis confirmed that the amino acid sequence of the humanized AC10 (hAC10) variable regions had the expected sequences. The resulting humanized AC10 $V_H$ and $V_L$ amino acid sequences had 92.3 and 89.3 percent homology (84.6 and 84.8 percent identity) with the corresponding murine AC10 $V_H$ and $V_L$ amino acid sequences, respectively. The human and murine $V_H$ and $V_L$ framework region amino acid sequences had 79.3 and 79.0 percent identity. The humanized AC10 $V_H$ and $V_L$ amino acid sequences had 85.5 and 86.8 percent homology (83.8 and 84.2 percent identity) with the corresponding human germline amino acid sequences, respectively.

Two framework positions were chosen for reintroduction of mouse donor residues. These were positions H71 and H91 in the $V_H$ domain, according to the Kabat numbering convention. No framework positions were altered in the $V_L$ domain, although mouse CDR1 residues at positions L25 and L33 were chosen for introduction of the human acceptor residue for that position.

Several variants of humanized AC10 were generated by incorporating different combinations of mouse framework donor residues in the $V_H$ domain or human CDR residues in the $V_L$ domain. These $V_H$ and $V_L$ domain variants are summarized below in Tables 2 and 3.

TABLE 2

| $V_H$ Variant | Donor Framework Residues | SEQ ID NO. |
|---|---|---|
| hV$_H$A | H71, H91 | 4 |
| hV$_H$B | H91 | 9 |
| hV$_H$C | H71 | 14 |
| hV$_H$D | none | 19 |

TABLE 3

| $V_L$ Variant | Acceptor CDR Residue | SEQ ID NO. |
|---|---|---|
| hV$_L$A | none | 26 |
| hV$_L$B | L25 | 31 |
| hV$_L$C | L33 | 36 |
| hV$_L$D | L25, L33 | 41 |

An alignment of AC10 $V_H$ humanized variants hVHa, hVHb, hVHc, and hVHd, with murine AC10 m$V_H$ and human germline $V_H$ exon $V_H$1-2 and $J_H$ exon $J_H$-4 is shown below in Table 4. Each residue is sequentially numbered according to its position as calculated using the Kabat numbering system.

TABLE 4

Heavy Chain Variable Domain

```
Sequential         10         20         30         40         50
Kabat #            10         20         30         40         50
mAC10 mVH     QIQLQQPGPE VVKPGASVKI SCKASGYTFT DYYITWVKQK PGQGLEWIGW
AC10 hVHa     QVQLVQSGAE VKKPGASVKV SCKASGYTFT DYYITWVRQA PGQGLEWMGW
AC10 hVHb     QVQLVQSGAE VKKPGASVKV SCKASGYTFT DYYITWVRQA PGQGLEWMGW
AC10 hVHc     QVQLVQSGAE VKKPGASVKV SCKASGYTFT DYYITWVRQA PGQGLEWMGW
AC10 hVHd     QVQLVQSGAE VKKPGASVKV SCKASGYTFT DYYITWVRQA PGQGLEWMGW
V_H1-2        QVQLVQSGAE VKKPGASVKV SCKASGYTFT -----WVRQA PGQGLEWMG-
Kabat                                           ^^^^^                ^
Chothia                                         ***** *****

Sequential         60         70         80         90        100
Kabat           a     60         70         80    abc    90
mAC10         IYPGSGNTKY NEKFKGKATL TVDTSSSTAF MQLSSLTSED TAVYFCANYG
AC10 hVHa     IYPGSGNTKY NEKFKGRVTM TVDTSISTAY MELSRLRSDD TAVYFCANYG
AC10 hVHb     IYPGSGNTKY NEKFKGRVTM TRDTSISTAY MELSRLRSDD TAVYFCANYG
AC10 hVHc     IYPGSGNTKY NEKFKGRVTM TVDTSISTAY MELSRLRSDD TAVYYCANYG
AC10 hVHd     IYPGSGNTKY NEKFKGRVTM TRDTSISTAY MELSRLRSDD TAVYYCANYG
V_H1-2        ---------- ------RVTM TRDTSISTAY MELSRLRSDD TAVYY-----
Kabat         ^^^^^^^^^^ ^^^^^^                                ^^^^^
Chothia       ******                                           **

Sequential        110
Kabat            100        110
mAC10         NYWFAYWGQG TQVTVSA    (SEQ ID NO: 2)
AC10 hVHa     NYWFAYWGQG TLVTVSS    (SEQ ID NO: 4)
AC10 hVHb     NYWFAYWGQG TLVTVSS    (SEQ ID NO: 9)
AC10 hVHc     NYWFAYWGQG TLVTVSS    (SEQ ID NO: 14)
AC10 hVHd     NYWFAYWGQG TLVTVSS    (SEQ ID NO: 19)
V_H1-2/J_H-4  --------QG TLVTVSS    (SEQ ID NO: 45)
Kabat         ^^^^^^^^^
Chothia       ******
```

An alignment of AC10 V_L humanized variants hVLa, hVLb, hVLc, and hVLd, with mAC10 mV_L and human germline Vκ exon B3 and Jκ exon Jκ-1 is shown below in Table 5. Each residue is sequentially numbered according to its position as calculated using the Kabat numbering system.

TABLE 5

Light Chain Variable Domain

```
Sequential         10         20         30         40         50
Kabat              10         20       abc d 30         40
mAC10         DIVLTQSPAS LAVSLGQRAT INCKASQSVD FDGDSYMNWY QQKPGQPPKV
AC10 hVLa     DIVMTQSPDS LAVSLGERAT INCKASQSVD FDGDSYMNWY QQKPGQPPKL
AC10 hVLb     DIVMTQSPDS LAVSLGERAT INCKSSQSVD FDGDSYMNWY QQKPGQPPKL
AC10 hVLc     DIVMTQSPDS LAVSLGERAT INCKASQSVD FDGDSYLNWY QQKPGQPPKL
AC10 hVLd     DIVMTQSPDS LAVSLGERAT INCKSSQSVD FDGDSYLNWY QQKPGQPPKL
VK B3         DIVMTQSPDS LAVSLGERAT INC------- --------WY QQKPGQPPKL
Kabat                                  ^^^^^^^ ^^^^^^^^
Chothia                                             ***** ******

Sequential         60         70         80         90        100
Kabat           50         60         70         80         90
mAC10         LIYAASNLES GIPARFSGSG SGTDFTLNIH PVEEEDAATY YCQQSNEDPW
AC10 hVLa     LIYAASNLES GVPDRFSGSG SGTDFTLTIS SLQAEDVAVY YCQQSNEDPW
AC10 hVLb     LIYAASNLES GVPDRFSGSG SGTDFTLTIS SLQAEDVAVY YCQQSNEDPW
AC10 hVLc     LIYAASNLES GVPDRFSGSG SGTDFTLTIS SLQAEDVAVY YCQQSNEDPW
AC10 hVLd     LIYAASNLES GVPDRFSGSG SGTDFTLTIS SLQAEDVAVY YCQQSNEDPW
VK B3         LIY------- GVPDRFSGSG SGTDFTLTIS SLQAEDVAVY YC--------
Kabat         ^^^^^^^                                       ^^^^^^^^
Chothia       ***                                               ******

Sequential        110
Kabat            100
mAC10         TFGGGTKLET K  (SEQ ID NO: 24)
AC10 hVLa     TFGQGTKVEI K  (SEQ ID NO: 26)
AC10 hVLb     TFGQGTKVEI K  (SEQ ID NO: 31)
AC10 hVLc     TFGQGTKVEI K  (SEQ ID NO: 36)
AC10 hVLd     TFGQGTKVEI K  (SEQ ID NO: 41)
VK B3/Jk-1    -FGQGTKVEI K  (SEQ ID NO: 46)
Kabat         ^
Chothia
```

Example 2

In Vitro Characterization of Humanized AC10 Variants

Combinations of heavy and light chain were co-expressed in 293 cells and Protein-A purified to generate the following variant antibodies comprising the indicated heavy and light chains: hAC10 HALA, hAC10 HALB, hAC10 HALC, hAC10 HALD, hAC10 HBLA, hAC10 HCLA, hAC10 HDLA and hAC10 HDLD.

The variants were tested for binding to CD30 surface antigen expressed on Karpas-299, an anaplastic large cell lymphoma cell line, using a competition binding assay in which cAC10, expressed in CHO cells, was europium labeled (see, e.g., Law et al., *Cancer Research* 65:8331-38 (2005)). The results, shown below in the second column of Table 6, indicate that all of the variants were able to compete with cAC10 for binding to CD30. Thus, the variants retained antigen binding activity.

Next, the variants were tested for in vitro cytotoxic activity against Karpas 299 as well as against a second CD30 positive cell line, L540. Variants were incubated for 92 hours with the cells in the presence of a crosslinking anti-human F(ab')$_2$ before the cells were labeled with [$^3$H]-thymidine. After a four-hour incubation, the cells were harvested and inhibition of DNA synthesis was assessed. Except for hAC10 HDLD, which had reduced activity on both cell lines tested, all other variants demonstrated cytotoxic activity against each of the cell lines comparable to control cAC10. The results are summarized in columns 3 and 4 of Table 6 below.

Additionally, vcMMAE conjugates (8 drugs/antibody) were made for selected antibody variants (see, e.g., Doronina et al., *Nature Biotechnology* 21:778-784 (2003)). These were tested in a cytotoxicity assay on CD30 expressing cell lines Karpas-299 and L540cy. Following a 92 hour incubation, resazurin was added and the cells were incubated for an additional four hours in the presence of resazurin. Cytotoxic activity was determined as assessed by dye reduction. cAC10 conjugated with vcMMAE at a ratio of 8 drugs per antibody (cAC10vcMMAE$_8$) and expressed in CHO or 293 cells served as control antibody-drug conjugates. The results, shown in columns 5 and 6 in Table 6 below, indicate that, in this assay, all variants tested were as potent as cAC10 conjugate controls.

TABLE 6

Summary of In Vitro Analysis of hAC10 variants

| Variant | Competition EC$_{50}$ (nM) Karpas 299 | In vitro cytotoxicity (crosslinked) IC$_{50}$ (ng/ml) Karpas 299 | | In vitro cytotoxicity (1° ADC-vcMMAE$_8$) IC$_{50}$ (ng/ml) | |
|---|---|---|---|---|---|
| | | Karpas 299 | L540cy | Karpas 299 | L540cy |
| hAC10 HALA | 6.61 | 4.18 | 5.85 | 2.4 | 8.4 |
| hAC10 HALB | 5.90 | 5.23 | 8.23 | nt | nt |
| hAC10 HALC | 3.53 | 2.16 | 5.52 | nt | nt |
| hAC10 HALD | 6.00 | 5.17 | 11.13 | nt | nt |
| hAC10 HBLA | 3.31 | 6.24 | 8.67 | 3.8 | 10.5 |
| hAC10 HCLA | 3.61 | 1.74 | 3.70 | 2.9 | 11.7 |
| hAC10 HDLA | 3.10 | 3.52 | 5.88 | 2.9 | 11.7 |
| hAC10 HDLD | 2.25 | 9.40 | 13.76 | nt | nt |
| cAC10 (CHO) | 2.90 | 2.70 | 5.82 | 2.2 | 12.6 |
| cAC10 (293) | nt | Nt | Nt | 2.2 | 8.9 |

"nt" means not tested.

Example 3

Pharmacokinetics of Humanized AC10

The pharmacokinetics of cAC10 and hAC10 HDLA were evaluated in SCID mice. SCID mice (n=3) were administered 10 mg/kg of test material by tail vein injection. Blood samples were collected from each mouse via the saphenous vein at 0.5 h, 4 h, 1d, 2 d, 4 d, 7 d, 14 d, 21d, 28 d, and 35 days post injection and serum was isolated. Serum concentrations of cAC10 and hAC10 HDLA were measured by antigen-binding ELISA.

FIG. 1 illustrates the pharmacokinetic profiles of cAC10 and hAC10. Phamacokinetic parameters were estimated by non-compartmental analysis using WinNonlin® (Pharsight Corp., Mountain View, Calif.). Similar clearance values of 8.3 and 75 ml/day/kg were observed for cAC10 and hAC10, respectively. The terminal half-lives of cAC10 and hAC10 were 17.5 and 13.9 days, respectively.

Example 4

In Vivo Efficacy of Humanized AC10

Figure 2:
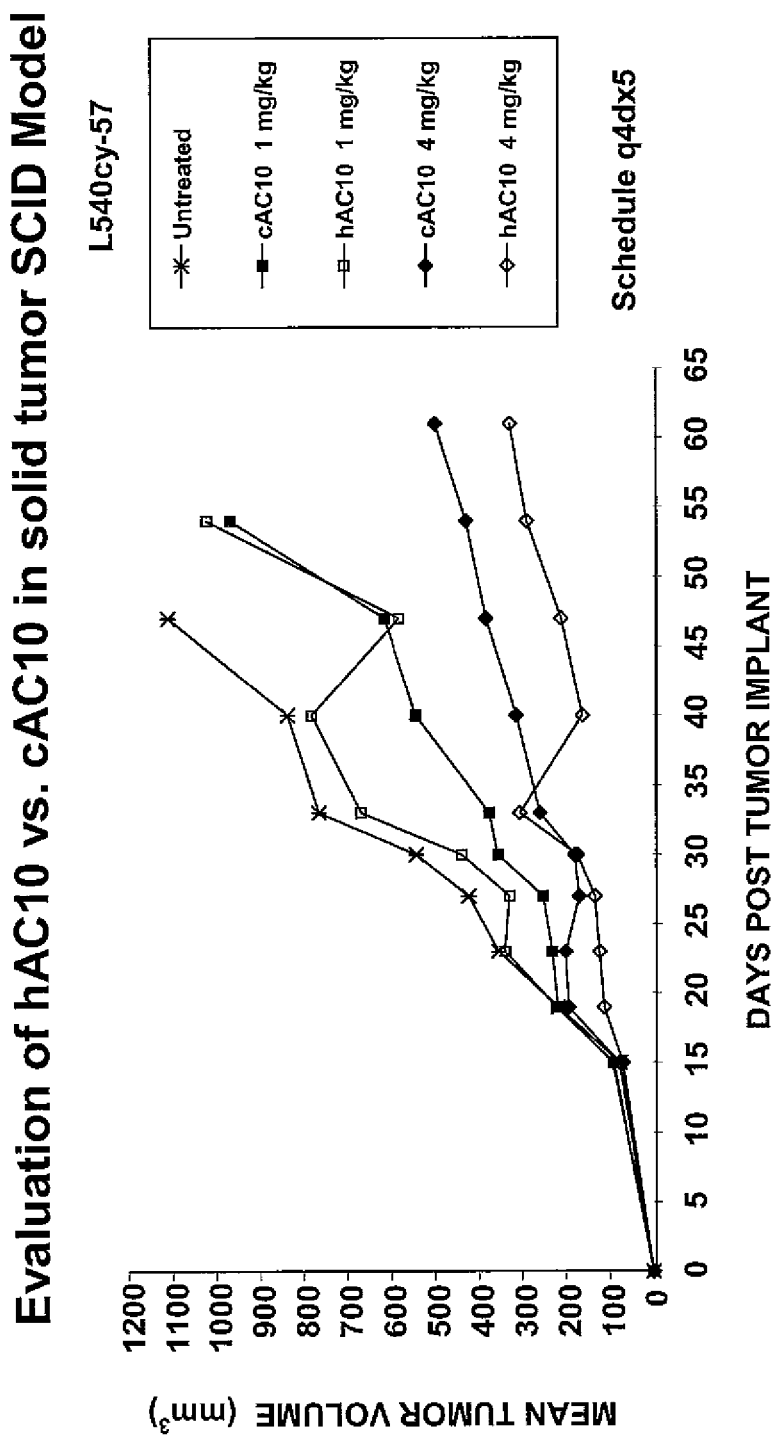
FIG. 2 illustrates the in vivo efficacy of cAC10 (chimeric AC10) antibody and a hAC10 (humanized AC10) antibody in a solid tumor SCID mouse model.

Five million L540cy cells were implanted into the right flank of C.B-17 SCID mice (Harlan, Indianapolis, Ind.) to establish a subcutaneous disease model of Hodgkin's disease. Therapy with antibodies was initiated when the tumor size in each group of animals averaged 100 mm$^3$. Treatment consisted of intravenous injections of 1 mg/Kg and 4 mg/Kg of cAC10 and hAC10 HDLA every fourth day for 5 injections. Tumor volume was calculated using the formula (length×width$^2$)/2. Animals were euthanized when tumor volumes reached approximately 1000 mm$^3$. Similar efficacy was observed for cAC10 and hAC10 at each dose as shown in FIG. 2.

ATCC DEPOSIT

Under the terms of the Budepest Treaty on the International Recognition of the Deposit of Microorganisms for the Purpose of Patent Procedure, the cell line producing antibody HDLA was deposited with the American Type Culture Collection (ATCC) on Aug. 22, 2005. The ATCC is located at 10801 University Boulevard, Manassas, Va. 20110-2209, USA. The ATCC deposit was given an accession number of PTA-6951 and the description of "hAC10 2-6D5." Any deposit is provided as a convenience to those of skill in the art and is not an admission that a deposit is required under 35 U.S.C. §112.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

No license is expressly or implicitly granted to any patent or patent applications referred to or incorporated herein. Various references, including patent applications, patents, and scientific publications, are cited herein, the disclosures of each of which is incorporated herein by reference in its entirety.

What is claimed is:

1. An isolated CD30 binding agent that specifically binds to human CD30, comprising:
   a heavy chain variable region comprising the amino acid sequence of SEQ ID NO:19, optionally comprising an amino acid substitution at position 71, position 91, or both positions 71 and 91, wherein the position is numbered according to the Kabat numbering system; and
   a light chain variable region comprising the amino acid sequence of SEQ ID NO:26, optionally comprising an amino acid substitution at position 25, position 33, or both positions 25 and 33, wherein the position is numbered according to the Kabat numbering system.

2. The CD30 binding agent of claim 1, wherein the CD30binding agent is conjugated to a cytotoxic agent.

3. The CD30 binding agent of claim 2, wherein the cytotoxic agent is auristatin E, MMAE or MMAF.

4. The CD30 binding agent of claim 2, wherein the cytotoxic agent is a chemotherapeutic agent.

5. The CD30 binding agent of claim 4, wherein the chemotherapeutic agent is MMAE.

6. The CD30 binding agent of claim 2, wherein the CD30 binding agent comprises a heavy chain variable region comprising the amino acid sequence of SEQ ID NO:19 and a light chain variable region comprising the amino acid sequence of SEQ ID NO:26.

7. The CD30 binding agent of claim 1, wherein the optional substitution at position 71 of the amino acid sequence of SEQ ID NO:19 is substitution of a valine residue in place of the arginine residue, the optional substitution at position 91 of the amino acid sequence of SEQ ID NO:19 is substitution of a phenylalanine residue in place of the tyrosine residue, the optional substitution at position 25 of the amino acid sequence of SEQ ID NO:26 is substitution of a serine residue in place of the alanine residue, and the optional substitution at position 33 of the amino acid sequence of SEQ ID NO:26 is substitution of a leucine residue in place of the methionine residue.

8. The CD30 binding agent of claim 7, wherein the heavy chain variable region comprises the amino acid sequence of SEQ ID NO:19 having a valine residue in place of the arginine residue at position 71 and a phenylalanine residue in place of the tyrosine residue at position 91.

9. The CD30 binding agent of claim 7, wherein the heavy chain variable region comprises the amino acid sequence of SEQ ID NO:19 having a phenylalanine residue in place of the tyrosine residue at position 91.

10. The CD30 binding agent of claim 7, wherein the heavy chain variable region comprises the amino acid sequence of SEQ ID NO:19 having a valine residue in place of the arginine residue at position 71.

11. The CD30 binding agent of claim 7, wherein the light chain variable region comprises the amino acid sequence of SEQ ID NO:26 having a serine residue in place of the alanine residue at position 25.

12. The CD30 binding agent of claim 7, wherein the light chain variable region comprises the amino acid sequence of SEQ ID NO:26 having a leucine residue in place of the methionine residue at position 33.

13. The CD30 binding agent of claim 7, wherein the light chain variable region comprises the amino acid sequence of SEQ ID NO:26 having a serine residue in place of the alanine residue at position 25 and having a leucine residue in place of the methionine residue at position 33.

14. The CD30 binding agent of claim 1, wherein the heavy chain variable region comprises the amino acid sequence of SEQ ID:19.

15. The CD30 binding agent of claim 1, wherein the light chain variable region comprises the amino acid sequence of SEQ ID NO:26.

16. A pharmaceutical composition comprising:
(i) the CD30 binding agent of claim 1; and
(ii) a pharmaceutically acceptable excipient.

17. The pharmaceutical composition of claim 16, wherein the antibody is conjugated to a cytotoxic, cytostatic or immunosuppressive agent.

18. The pharmaceutical composition of claim 16, wherein the CD30 binding agent comprises a heavy chain variable region comprising the amino acid sequence of SEQ ID NO:19 and a light chain variable region comprising the amino acid sequence of SEQ ID NO:26.

19. An isolated CD30 binding agent that specifically binds to human CD30, comprising a heavy chain variable region and a light chain variable region, wherein the heavy chain variable region comprises the amino acid sequence of SEQ ID NO:19 and the light chain variable region comprises the amino acid sequence of SEQ ID NO:26.

20. The CD30 binding agent of claim 19, further comprising a human IgG constant region joined to the heavy chain variable region and a human light chain constant domain joined to the light chain variable region.

21. The CD30 binding agent of claim 20, wherein the human IgG constant domain is human IgG1, and the human light chain constant domain is human κ(kappa).

22. The CD30 binding agent of claim 21, wherein the heavy chain comprises the amino acid sequence of SEQ ID NO:22 and the light chain comprises the amino acid sequence of SEQ ID NO:29.

* * * * *

SEQUENCE LISTING

<160> NUMBER OF SEQ ID NOS: 46

<210> SEQ ID NO 1
<211> LENGTH: 351
<212> TYPE: DNA
<213> ORGANISM: Mus musculus

<400> SEQUENCE: 1
caggtgcagc tggtgcagtc tggagccgag gtgaagaagc ctggggcttc agtgaaggtg     60
tcctgcaagg cttctggcta caccttcact gactactata taacctgggt gaggcaggcc    120
cctggacagg gacttgagtg gatgggatgg atttatcctg gaagcggtaa tactaagtac    180
aatgagaagt tcaagggcag ggtgacaatg actgtagaca catccatcag cacagcctac    240
atggagctca gcagactgag gtctgacgac actgctgtct atttctgtgc gaactatggt    300
aactactggt ttgcttactg gggccaaggg actctggtca ctgtctcttc c              351

<210> SEQ ID NO 2
<211> LENGTH: 117
<212> TYPE: PRT
<213> ORGANISM: Mus musculus

<400> SEQUENCE: 2

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala
        115

<210> SEQ ID NO 3
<211> LENGTH: 351
<212> TYPE: DNA
<213> ORGANISM: Artificial
<220> FEATURE:
<223> OTHER INFORMATION: Synthetic

<400> SEQUENCE: 3
caggtgcagc tggtgcagtc tggagccgag gtgaagaagc ctggggcttc agtgaaggtg     60
tcctgcaagg cttctggcta caccttcact gactactata taacctgggt gaggcaggcc    120
cctggacagg gacttgagtg gatgggatgg atttatcctg gaagcggtaa tactaagtac    180
aatgagaagt tcaagggcag ggtgacaatg actgtagaca catccatcag cacagcctac    240
atggagctca gcagactgag gtctgacgac actgctgtct atttctgtgc gaactatggt    300
aactactggt ttgcctactg gggccaaggg actctggtca ctgtctcttc c              351

<210> SEQ ID NO 4

```
<211> LENGTH: 117
<212> TYPE: PRT
<213> ORGANISM: Artificial
<220> FEATURE:
<223> OTHER INFORMATION: Synthetic

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 5
<211> LENGTH: 1401
<212> TYPE: DNA
<213> ORGANISM: Artificial
<220> FEATURE:
<223> OTHER INFORMATION: Synthetic

<400> SEQUENCE: 5
atgggatgga gctggatctt tcttttcctc ctgtcaggaa ctgcaggtgt ccattgtcag    60
gtgcagctgg tgcagtctgg agccgaggtg aagaagcctg ggcttcagt gaaggtgtcc   120 tgcaaggctt ctggctacac cttcactgac tactatataa cctgggtgag gcaggcccct   180
ggacagggac ttgagtggat gggatggatt tatcctggaa gcggtaatac taagtacaat   240
gagaagttca agggcagggt gacaatgact gtagacacat ccatcagcac agcctacatg   300
gagctcagca gactgaggtc tgacgacact gctgtctatt tctgtgcgaa ctatggtaac   360
tactggtttg cctactgggg ccaagggact ctggtcactg tctcttccgc tagcaccaag   420
ggcccatcgg tcttccccct ggcaccctcc tccaagagca cctctggggg cacagcggcc   480
ctgggctgcc tggtcaagga ctacttcccc gaaccggtga cggtgtcgtg gaactcaggc   540
gccctgacca gcggcgtgca caccttcccg gctgtcctac agtcctcagg actctactcc   600
ctcagcagcg tggtgaccgt gccctccagc agcttgggca cccagaccta catctgcaac   660
gtgaatcaca agcccagcaa caccaaggtg gacaagaaag ttgagcccaa atcttgtgac   720
aaaactcaca catgcccacc gtgcccagca cctgaactcc tggggggacc gtcagtcttc   780
ctcttccccc caaaacccaa ggacaccctc atgatctccc ggacccctga ggtcacatgc   840
gtggtggtgg acgtgagcca cgaagaccct gaggtcaagt tcaactggta cgtggacggc   900
gtggaggtgc ataatgccaa gacaaagccg cgggaggagc agtacaacag cacgtaccgt   960
gtggtcagcg tcctcaccgt cctgcaccag gactggctga atggcaagga gtacaagtgc  1020
aaggtctcca acaaagccct cccagccccc atcgagaaaa ccatctccaa agccaagggg  1080
cagccccgag aaccacaggt gtacaccctg cccccatccc gggatgagct gaccaagaac  1140
```

-continued

```
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg a                                              1401
```

```
<210> SEQ ID NO 6
<211> LENGTH: 466
<212> TYPE: PRT
<213> ORGANISM: Artificial
<220> FEATURE:
<223> OTHER INFORMATION: Synthetic

<400> SEQUENCE: 6
```

| Met | Gly | Trp | Ser | Trp | Ile | Phe | Leu | Phe | Leu | Leu | Ser | Gly | Thr | Ala | Gly |
|---|---|---|---|---|---|---|---|---|---|---|---|---|---|---|---|
| 1 | | | | 5 | | | | | 10 | | | | | 15 | |

| Val | His | Cys | Gln | Val | Gln | Leu | Val | Gln | Ser | Gly | Ala | Glu | Val | Lys | Lys |
|---|---|---|---|---|---|---|---|---|---|---|---|---|---|---|---|
| | | | 20 | | | | | 25 | | | | | 30 | | |

| Pro | Gly | Ala | Ser | Val | Lys | Val | Ser | Cys | Lys | Ala | Ser | Gly | Tyr | Thr | Phe |
|---|---|---|---|---|---|---|---|---|---|---|---|---|---|---|---|
| | | 35 | | | | | 40 | | | | | 45 | | | |

| Thr | Asp | Tyr | Tyr | Ile | Thr | Trp | Val | Arg | Gln | Ala | Pro | Gly | Gln | Gly | Leu |
|---|---|---|---|---|---|---|---|---|---|---|---|---|---|---|---|
| | 50 | | | | | 55 | | | | | 60 | | | | |

| Glu | Trp | Met | Gly | Trp | Ile | Tyr | Pro | Gly | Ser | Asn | Thr | Lys | Tyr | Asn |
|---|---|---|---|---|---|---|---|---|---|---|---|---|---|---|
| 65 | | | | | 70 | | | | | 75 | | | | | 80 |

| Glu | Lys | Phe | Lys | Gly | Arg | Val | Thr | Met | Thr | Val | Asp | Thr | Ser | Ile | Ser |
|---|---|---|---|---|---|---|---|---|---|---|---|---|---|---|---|
| | | | | 85 | | | | | 90 | | | | | 95 | |

| Thr | Ala | Tyr | Met | Glu | Leu | Ser | Arg | Leu | Arg | Ser | Asp | Asp | Thr | Ala | Val |
|---|---|---|---|---|---|---|---|---|---|---|---|---|---|---|---|
| | | | 100 | | | | | 105 | | | | | 110 | | |

| Tyr | Phe | Cys | Ala | Asn | Tyr | Gly | Asn | Tyr | Trp | Phe | Ala | Tyr | Trp | Gly | Gln |
|---|---|---|---|---|---|---|---|---|---|---|---|---|---|---|---|
| | | 115 | | | | | 120 | | | | | 125 | | | |

| Gly | Thr | Leu | Val | Thr | Val | Ser | Ser | Ala | Ser | Thr | Lys | Gly | Pro | Ser | Val |
|---|---|---|---|---|---|---|---|---|---|---|---|---|---|---|---|
| | 130 | | | | | 135 | | | | | 140 | | | | |

| Phe | Pro | Leu | Ala | Pro | Ser | Ser | Lys | Ser | Thr | Ser | Gly | Gly | Thr | Ala | Ala |
|---|---|---|---|---|---|---|---|---|---|---|---|---|---|---|---|
| 145 | | | | | 150 | | | | | 155 | | | | | 160 |

| Leu | Gly | Cys | Leu | Val | Lys | Asp | Tyr | Phe | Pro | Glu | Pro | Val | Thr | Val | Ser |
|---|---|---|---|---|---|---|---|---|---|---|---|---|---|---|---|
| | | | | 165 | | | | | 170 | | | | | 175 | |

| Trp | Asn | Ser | Gly | Ala | Leu | Thr | Ser | Gly | Val | His | Thr | Phe | Pro | Ala | Val |
|---|---|---|---|---|---|---|---|---|---|---|---|---|---|---|---|
| | | | 180 | | | | | 185 | | | | | 190 | | |

| Leu | Gln | Ser | Ser | Gly | Leu | Tyr | Ser | Leu | Ser | Ser | Val | Val | Thr | Val | Pro |
|---|---|---|---|---|---|---|---|---|---|---|---|---|---|---|---|
| | | 195 | | | | | 200 | | | | | 205 | | | |

| Ser | Ser | Ser | Leu | Gly | Thr | Gln | Thr | Tyr | Ile | Cys | Asn | Val | Asn | His | Lys |
|---|---|---|---|---|---|---|---|---|---|---|---|---|---|---|---|
| | 210 | | | | | 215 | | | | | 220 | | | | |

| Pro | Ser | Asn | Thr | Lys | Val | Asp | Lys | Lys | Val | Glu | Pro | Lys | Ser | Cys | Asp |
|---|---|---|---|---|---|---|---|---|---|---|---|---|---|---|---|
| 225 | | | | | 230 | | | | | 235 | | | | | 240 |

| Lys | Thr | His | Thr | Cys | Pro | Pro | Cys | Pro | Ala | Pro | Glu | Leu | Leu | Gly | Gly |
|---|---|---|---|---|---|---|---|---|---|---|---|---|---|---|---|
| | | | | 245 | | | | | 250 | | | | | 255 | |

| Pro | Ser | Val | Phe | Leu | Phe | Pro | Pro | Lys | Pro | Lys | Asp | Thr | Leu | Met | Ile |
|---|---|---|---|---|---|---|---|---|---|---|---|---|---|---|---|
| | | | 260 | | | | | 265 | | | | | 270 | | |

| Ser | Arg | Thr | Pro | Glu | Val | Thr | Cys | Val | Val | Val | Asp | Val | Ser | His | Glu |
|---|---|---|---|---|---|---|---|---|---|---|---|---|---|---|---|
| | | 275 | | | | | 280 | | | | | 285 | | | |

| Asp | Pro | Glu | Val | Lys | Phe | Asn | Trp | Tyr | Val | Asp | Gly | Val | Glu | Val | His |
|---|---|---|---|---|---|---|---|---|---|---|---|---|---|---|---|
| | 290 | | | | | 295 | | | | | 300 | | | | |

| Asn | Ala | Lys | Thr | Lys | Pro | Arg | Glu | Glu | Gln | Tyr | Asn | Ser | Thr | Tyr | Arg |
|---|---|---|---|---|---|---|---|---|---|---|---|---|---|---|---|
| 305 | | | | | 310 | | | | | 315 | | | | | 320 |

```
Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
            450                 455                 460

Gly Lys
465

<210> SEQ ID NO 7
<211> LENGTH: 447
<212> TYPE: PRT
<213> ORGANISM: Artificial
<220> FEATURE:
<223> OTHER INFORMATION: Synthetic

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
50                  55                  60

Lys Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
            85                  90                  95

Ala Asn Tyr Gly Asn Tyr Trp Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
```

```
              210                 215                 220
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 8
<211> LENGTH: 351
<212> TYPE: DNA
<213> ORGANISM: Artificial
<220> FEATURE:
<223> OTHER INFORMATION: Synthetic

<400> SEQUENCE: 8
caggtgcagc tggtgcagtc tggagccgag gtgaagaagc ctggggcttc agtgaaggtg      60
tcctgcaagg cttctggcta caccttcact gactactata taacctgggt gaggcaggcc    120
cctggacagg gacttgagtg gatgggatgg atttatcctg gaagcggtaa tactaagtac    180
aatgagaagt tcaagggcag ggtgacaatg actcgggaca catccatcag cacagcctac    240
atggagctca gcagactgag gtctgacgac actgctgtct atttctgtgc gaactatggt    300
aactactggt ttgcttactg gggccaaggg actctggtca ctgtctcttc c             351

<210> SEQ ID NO 9
<211> LENGTH: 117
<212> TYPE: PRT
<213> ORGANISM: Artificial
<220> FEATURE:
<223> OTHER INFORMATION: Synthetic

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
```

```
                    20                  25                  30
Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 10
<211> LENGTH: 1401
<212> TYPE: DNA
<213> ORGANISM: Artificial
<220> FEATURE:
<223> OTHER INFORMATION: Synthetic

<400> SEQUENCE: 10
atgggatgga gctggatctt tcttttcctc ctgtcaggaa ctgcaggtgt ccattgtcag      60
gtgcagctgg tgcagtctgg agccgaggtg aagaagcctg ggcttcagt gaaggtgtcc     120 tgcaaggctt ctggctacac cttcactgac tactatataa cctgggtgag gcaggcccct    180
ggacagggac ttgagtggat gggatggatt tatcctggaa gcggtaatac taagtacaat    240
gagaagttca agggcaggt gacaatgact cgggacacat ccatcagcac agcctacatg     300
gagctcagca gactgaggtc tgacgacact gctgtctatt tctgtgcgaa ctatggtaac    360
tactggtttg cttactgggg ccaagggact ctggtcactg tctcttccgc tagcaccaag    420
ggcccatcgg tcttccccct ggcaccctcc tccaagagca cctctggggg cacagcggcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagaaag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggatgagct gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                              1401

<210> SEQ ID NO 11
```

```
<211> LENGTH: 466
<212> TYPE: PRT
<213> ORGANISM: Artificial
<220> FEATURE:
<223> OTHER INFORMATION: Synthetic

<400> SEQUENCE: 11

Met Gly Trp Ser Trp Ile Phe Leu Phe Leu Leu Ser Gly Thr Ala Gly
1               5                   10                  15

Val His Cys Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Tyr Ile Thr Trp Val Arg Gln Ala Pro Gly Gln Gly Leu
    50                  55                  60

Glu Trp Met Gly Trp Ile Tyr Pro Gly Ser Gly Asn Thr Lys Tyr Asn
65                  70                  75                  80

Glu Lys Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Phe Cys Ala Asn Tyr Gly Asn Tyr Trp Phe Ala Tyr Trp Gly Gln
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
370                 375                 380
```

```
Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
        420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
450                 455                 460

Gly Lys
465

<210> SEQ ID NO 12
<211> LENGTH: 447
<212> TYPE: PRT
<213> ORGANISM: Artificial
<220> FEATURE:
<223> OTHER INFORMATION: Synthetic

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
```

```
                 275                 280                 285
Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 13
<211> LENGTH: 351
<212> TYPE: DNA
<213> ORGANISM: Artificial
<220> FEATURE:
<223> OTHER INFORMATION: Synthetic

<400> SEQUENCE: 13
caggtgcagc tggtgcagtc tggagccgag gtgaagaagc ctggggcttc agtgaaggtg      60
tcctgcaagg cttctggcta caccttcact gactactata taacctgggt gaggcaggcc    120
cctggacagg gacttgagtg gatgggatgg atttatcctg gaagcggtaa tactaagtac    180
aatgagaagt tcaagggcag ggtgacaatg actgtagaca catccatcag cacagcctac    240
atggagctca gcagactgag gtctgacgac actgctgtct attactgtgc gaactatggt    300
aactactggt ttgcttactg gggccaaggg actctggtca ctgtctcttc c             351

<210> SEQ ID NO 14
<211> LENGTH: 117
<212> TYPE: PRT
<213> ORGANISM: Artificial
<220> FEATURE:
<223> OTHER INFORMATION: Synthetic

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
```

```
                    85                  90                  95
Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 15
<211> LENGTH: 1401
<212> TYPE: DNA
<213> ORGANISM: Artificial
<220> FEATURE:
<223> OTHER INFORMATION: Synthetic

<400> SEQUENCE: 15
atgggatgga gctggatctt tcttttcctc ctgtcaggaa ctgcaggtgt ccattgtcag     60
gtgcagctgg tgcagtctgg agccgaggtg aagaagcctg ggcttcagt  gaaggtgtcc    120 tgcaaggctt ctggctacac cttcactgac tactatataa cctgggtgag gcaggcccct    180
ggacagggac ttgagtggat gggatggatt tatcctggaa gcggtaatac taagtacaat    240
gagaagttca gggcagggt  gacaatgact gtagacacat ccatcagcac agcctacatg    300
gagctcagca gactgaggtc tgacgacact gctgtctatt actgtgcgaa ctatggtaac    360
tactggtttg cttactgggg ccaagggact ctggtcactg tctcttccgc tagcaccaag    420
ggcccatcgg tcttcccct  ggcaccctcc tccaagagca cctctggggg cacagcggcc    480
ctgggctgcc tggtcaagga ctacttcccc gaaccggtga cggtgtcgtg gaactcaggc    540
gccctgacca gcggcgtgca ccttcccg   ctgtcctac  agtcctcagg actctactcc    600
ctcagcagcg tggtgaccgt gccctccagc agcttgggca cccagaccta catctgcaac    660
gtgaatcaca agcccagcaa caccaaggtg gacaagaaag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggatgagct gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                             1401

<210> SEQ ID NO 16
<211> LENGTH: 466
<212> TYPE: PRT
<213> ORGANISM: Artificial
<220> FEATURE:
<223> OTHER INFORMATION: Synthetic

<400> SEQUENCE: 16

Met Gly Trp Ser Trp Ile Phe Leu Phe Leu Leu Ser Gly Thr Ala Gly
1               5                   10                  15

Val His Cys Gln Val Gln Leu Val Gln Ser Gly Ala Glu Val Lys Lys
```

```
                    20                  25                  30
Pro Gly Ala Ser Val Lys Val Ser Cys Lys Ala Ser Gly Tyr Thr Phe
                35                  40                  45
Thr Asp Tyr Tyr Ile Thr Trp Val Arg Gln Ala Pro Gly Gln Gly Leu
50                  55                  60
Glu Trp Met Gly Trp Ile Tyr Pro Gly Ser Gly Asn Thr Lys Tyr Asn
65                  70                  75                  80
Glu Lys Phe Lys Gly Arg Val Thr Met Thr Val Asp Thr Ser Ile Ser
                85                  90                  95
Thr Ala Tyr Met Glu Leu Ser Arg Leu Arg Ser Asp Asp Thr Ala Val
                100                 105                 110
Tyr Tyr Cys Ala Asn Tyr Gly Asn Tyr Trp Phe Ala Tyr Trp Gly Gln
                115                 120                 125
Gly Thr Leu Val Thr Val Ser Ser Ala Ser Thr Lys Gly Pro Ser Val
    130                 135                 140
Phe Pro Leu Ala Pro Ser Ser Lys Ser Thr Ser Gly Gly Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
                180                 185                 190
Leu Gln Ser Ser Gly Leu Tyr Ser Leu Ser Ser Val Val Thr Val Pro
                195                 200                 205
Ser Ser Ser Leu Gly Thr Gln Thr Tyr Ile Cys Asn Val Asn His Lys
    210                 215                 220
Pro Ser Asn Thr Lys Val Asp Lys Lys Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
                260                 265                 270
Ser Arg Thr Pro Glu Val Thr Cys Val Val Val Asp Val Ser His Glu
    275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
                340                 345                 350
Lys Thr Ile Ser Lys Ala Lys Gly Gln Pro Arg Glu Pro Gln Val Tyr
                355                 360                 365
Thr Leu Pro Pro Ser Arg Asp Glu Leu Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
                420                 425                 430
Lys Ser Arg Trp Gln Gln Gly Asn Val Phe Ser Cys Ser Val Met His
                435                 440                 445
```

Glu Ala Leu His Asn His Tyr Thr Gln Lys Ser Leu Ser Leu Ser Pro
            450                 455                 460
Gly Lys
465

<210> SEQ ID NO 17
<211> LENGTH: 447
<212> TYPE: PRT
<213> ORGANISM: Artificial
<220> FEATURE:
<223> OTHER INFORMATION: Synthetic

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro

```
                    340             345             350
Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 18
<211> LENGTH: 351
<212> TYPE: DNA
<213> ORGANISM: Artificial
<220> FEATURE:
<223> OTHER INFORMATION: Synthetic

<400> SEQUENCE: 18
caggtgcagc tggtgcagtc tggagccgag gtgaagaagc ctggggcttc agtgaaggtg      60
tcctgcaagg cttctggcta caccttcact gactactata taacctgggt gaggcaggcc    120
cctggacagg gacttgagtg gatgggatgg atttatcctg gaagcggtaa tactaagtac    180
aatgagaagt tcaagggcag ggtgacaatg actcgggaca catccatcag cacagcctac    240
atggagctca gcagactgag gtctgacgac actgctgtct attactgtgc gaactatggt    300
aactactggt ttgcctactg gggccaaggg actctggtca ctgtctcttc c              351

<210> SEQ ID NO 19
<211> LENGTH: 117
<212> TYPE: PRT
<213> ORGANISM: Artificial
<220> FEATURE:
<223> OTHER INFORMATION: Synthetic

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 20
<211> LENGTH: 1401
<212> TYPE: DNA
```

```
<213> ORGANISM: Artificial
<220> FEATURE:
<223> OTHER INFORMATION: Synthetic

<400> SEQUENCE: 20
atgggatgga gctggatctt tcttttcctc ctgtcaggaa ctgcaggtgt ccattgtcag        60
gtgcagctgg tgcagtctgg agccgaggtg aagaagcctg gggcttcagt gaaggtgtcc      120
tgcaaggctt ctggctacac cttcactgac tactatataa cctgggtgag gcaggcccct      180
ggacagggac ttgagtggat gggatggatt tatcctggaa gcggtaatac taagtacaat      240
gagaagttca agggcagggt gacaatgact cgggacacat ccatcagcac agcctacatg      300
gagctcagca gactgaggtc tgacgacact gctgtctatt actgtgcgaa ctatggtaac      360
tactggtttg cctactgggg ccaagggact ctggtcactg tctcttccgc tagcaccaag      420
ggcccatcgg tcttccccct ggcaccctcc tccaagagca cctctggggg cacagcggcc      480
ctgggctgcc tggtcaagga ctacttcccc gaaccggtga cggtgtcgtg gaactcaggc      540
gccctgacca gcggcgtgca caccttcccg gctgtcctac agtcctcagg actctactcc      600
ctcagcagcg tggtgaccgt gccctccagc agcttgggca cccagaccta catctgcaac      660
gtgaatcaca agcccagcaa caccaaggtg gacaagaaag ttgagcccaa atcttgtgac      720
aaaactcaca catgcccacc gtgcccagca cctgaactcc tggggggacc gtcagtcttc      780
ctcttccccc caaaacccaa ggacaccctc atgatctccc ggacccctga ggtcacatgc      840
gtggtggtgg acgtgagcca cgaagaccct gaggtcaagt tcaactggta cgtggacggc      900
gtggaggtgc ataatgccaa gacaaagccg cgggaggagc agtacaacag cacgtaccgt      960
gtggtcagcg tcctcaccgt cctgcaccag gactggctga atggcaagga gtacaagtgc     1020
aaggtctcca acaaagccct cccagccccc atcgagaaaa ccatctccaa agccaaaggg     1080
cagccccgag aaccacaggt gtacaccctg cccccatccc gggatgagct gaccaagaac     1140
caggtcagcc tgacctgcct ggtcaaaggc ttctatccca gcgacatcgc cgtggagtgg     1200
gagagcaatg ggcagccgga gaacaactac aagaccacgc ctcccgtgct ggactccgac     1260
ggctccttct tcctctacag caagctcacc gtggacaaga gcaggtggca gcaggggaac     1320
gtcttctcat gctccgtgat gcatgaggct ctgcacaacc actacacgca gaagagcctc     1380
tccctgtctc cgggtaaatg a                                                1401

<210> SEQ ID NO 21
<211> LENGTH: 466
<212> TYPE: PRT
<213> ORGANISM: Artificial
<220> FEATURE:
<223> OTHER INFORMATION: Synthetic

<400> SEQUENCE: 21

Met Gly Trp Ser Trp Ile Phe Leu Phe Leu Leu Ser Gly Thr Ala Gly
1               5                   10                  15

Val His Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Tyr Ile Thr Trp Val Arg Gln Ala Pro Gly Gln Gly Leu
    50                  55                  60

Glu Trp Met Gly Trp Ile Tyr Pro Gly Ser Gly Asn Thr Lys Tyr Asn
65                  70                  75                  80

Glu Lys Phe Lys Gly Arg Val Thr Met Thr Arg Asp Thr Ser Ile Ser
```

```
                    85                  90                  95
Thr Ala Tyr Met Glu Leu Ser Arg Leu Arg Ser Asp Asp Thr Ala Val
            100                 105                 110
Tyr Tyr Cys Ala Asn Tyr Gly Asn Tyr Trp Phe Ala Tyr Trp Gly Gln
        115                 120                 125
Gly Thr Leu Val Thr Val Ser Ser Ala Ser Thr Lys Gly Pro Ser Val
    130                 135                 140
Phe Pro Leu Ala Pro Ser Ser Lys Ser Thr Ser Gly Gly Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
            180                 185                 190
Leu Gln Ser Ser Gly Leu Tyr Ser Leu Ser Ser Val Val Thr Val Pro
        195                 200                 205
Ser Ser Ser Leu Gly Thr Gln Thr Tyr Ile Cys Asn Val Asn His Lys
    210                 215                 220
Pro Ser Asn Thr Lys Val Asp Lys Lys Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Asp Glu Leu Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 22
<211> LENGTH: 447
<212> TYPE: PRT
<213> ORGANISM: Artificial
<220> FEATURE:
```

<223> OTHER INFORMATION: Synthetic

<400> SEQUENCE: 22

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
```

```
                        405                 410                 415
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 23
<211> LENGTH: 333
<212> TYPE: DNA
<213> ORGANISM: Mus musculus

<400> SEQUENCE: 23
gacattgtga tgacccaatc tccagactct ttggctgtgt ctctagggga gagggccacc      60
atcaactgca gtccagcca  aagtgttgat tttgatggtg atagttatct gaactggtac     120
caacagaaac caggacagcc acccaaactg ctcatctatg ctgcatccaa tctggaatct     180
ggggtgccag acaggtttag tggcagtggg tctgggacag acttcaccct caccatcagc     240
tccctgcagg ccgaggatgt ggcagtgtat tactgtcagc aaagtaatga ggatccgtgg     300
acgttcggtc aggcaccaa  ggtggaaatc aaa                                  333

<210> SEQ ID NO 24
<211> LENGTH: 111
<212> TYPE: PRT
<213> ORGANISM: Mus musculus

<400> SEQUENCE: 24

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 25
<211> LENGTH: 336
<212> TYPE: DNA
<213> ORGANISM: Artificial
<220> FEATURE:
<223> OTHER INFORMATION: Synthetic

<400> SEQUENCE: 25
gacattgtga tgacccaatc tccagactct ttggctgtgt ctctagggga gagggccacc      60
atcaactgca aggccagcca aagtgttgat tttgatggtg atagttatat gaactggtac     120
caacagaaac caggacagcc acccaaactg ctcatctatg ctgcatccaa tctggaatct     180
ggggtgccag acaggtttag tggcagtggg tctgggacag acttcaccct caccatcagc     240
tccctgcagg ccgaggatgt ggcagtgtat tactgtcagc aaagtaatga ggatccgtgg     300
acgttcggtc aggcaccaa  ggtggaaatc aaacga                               336
```

```
<210> SEQ ID NO 26
<211> LENGTH: 111
<212> TYPE: PRT
<213> ORGANISM: Artificial
<220> FEATURE:
<223> OTHER INFORMATION: Synthetic

<400> SEQUENCE: 26
```

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys
            100                 105                 110

```
<210> SEQ ID NO 27
<211> LENGTH: 717
<212> TYPE: DNA
<213> ORGANISM: Artificial
<220> FEATURE:
<223> OTHER INFORMATION: Synthetic

<400> SEQUENCE: 27
```
atggagacag acacaatcct gctatgggtg ctgctgctct gggttccagg ctccactggt      60
gacattgtga tgacccaatc tccagactct ttggctgtgt ctctagggga gagggccacc     120
atcaactgca aggccagcca agtgttgat tttgatggtg atagttatat gaactggtac     180
caacagaaac aggacagcc acccaaactg ctcatctatg ctgcatccaa tctggaatct     240
ggggtgccag acaggtttag tggcagtggg tctgggacag acttcaccct caccatcagc     300
tccctgcagg ccgaggatgt ggcagtgtat tactgtcagc aaagtaatga ggatccgtgg     360
acgttcggtc agggcaccaa ggtggaaatc aaacgaactg tggcggcgcc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660 acccatcagg gcctgagctc gcccgtcaca aagagcttca caggggaga gtgttag       717

```
<210> SEQ ID NO 28
<211> LENGTH: 238
<212> TYPE: PRT
<213> ORGANISM: Artificial
<220> FEATURE:
<223> OTHER INFORMATION: Synthetic

<400> SEQUENCE: 28
```

Met Glu Thr Asp Thr Ile Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Lys Ala Ser Gln Ser
        35                  40                  45

Val Asp Phe Asp Gly Asp Ser Tyr Met Asn Trp Tyr Gln Gln Lys Pro
 50                  55                  60

Gly Gln Pro Pro Lys Leu Leu Ile Tyr Ala Ala Ser Asn Leu Glu Ser
 65                  70                  75                  80

Gly Val Pro Asp Arg Phe Ser Gly Ser Gly Ser Gly Thr Asp Phe Thr
                 85                  90                  95

Leu Thr Ile Ser Ser Leu Gln Ala Glu Asp Val Ala Val Tyr Tyr Cys
            100                 105                 110

Gln Gln Ser Asn Glu Asp Pro Trp Thr Phe Gly Gln Gly Thr Lys Val
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 29
<211> LENGTH: 218
<212> TYPE: PRT
<213> ORGANISM: Artificial
<220> FEATURE:
<223> OTHER INFORMATION: Synthetic

<400> SEQUENCE: 29

Asp Ile Val Met Thr Gln Ser Pro Asp Ser Leu Ala Val Ser Leu Gly
 1               5                  10                  15

Glu Arg Ala Thr Ile Asn Cys Lys Ala Ser Gln Ser Val Asp Phe Asp
                 20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr

```
                165                 170                 175
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 30
<211> LENGTH: 336
<212> TYPE: DNA
<213> ORGANISM: Artificial
<220> FEATURE:
<223> OTHER INFORMATION: Synthetic

<400> SEQUENCE: 30
gacattgtga tgacccaatc tccagactct ttggctgtgt ctctagggga gagggccacc    60
atcaactgca agtccagcca agtgttgat tttgatggtg atagttatat gaactggtac   120
caacagaaac aggacagcc acccaaactg ctcatctatg ctgcatccaa tctggaatct   180
ggggtgccag acaggtttag tggcagtggg tctgggacag acttcaccct caccatcagc   240
tccctgcagg ccgaggatgt ggcagtgtat tactgtcagc aaagtaatga ggatccgtgg   300
acgttcggtc agggcaccaa ggtggaaatc aaacga                              336

<210> SEQ ID NO 31
<211> LENGTH: 111
<212> TYPE: PRT
<213> ORGANISM: Artificial
<220> FEATURE:
<223> OTHER INFORMATION: Synthetic

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys
            100                 105                 110

<210> SEQ ID NO 32
<211> LENGTH: 714
<212> TYPE: DNA
<213> ORGANISM: Artificial
<220> FEATURE:
<223> OTHER INFORMATION: Synthetic

<400> SEQUENCE: 32
atggagacag acacaatcct gctatgggtg ctgctgctct gggttccagg ctccactggt    60
gacattgtga tgacccaatc tccagactct ttggctgtgt ctctagggga gagggccacc   120
atcaactgca agtccagcca agtgttgat tttgatggtg atagttatat gaactggtac   180
```

```
caacagaaac caggacagcc acccaaactg ctcatctatg ctgcatccaa tctggaatct    240
ggggtgccag acaggtttag tggcagtggg tctgggacag acttcaccct caccatcagc    300
tccctgcagg ccgaggatgt ggcagtgtat tactgtcagc aaagtaatga ggatccgtgg    360
acgttcggtc agggcaccaa ggtggaaatc aaacgaactg tggcggcgcc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc    660 acccatcagg gcctgagctc gcccgtcaca aagagcttca cagggga gtgt             714
```

<210> SEQ ID NO 33
<211> LENGTH: 238
<212> TYPE: PRT
<213> ORGANISM: Artificial
<220> FEATURE:
<223> OTHER INFORMATION: Synthetic

<400> SEQUENCE: 33

```
Met Glu Thr Asp Thr Ile Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Asp Phe Asp Gly Asp Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ser Asn Glu Asp Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 34
<211> LENGTH: 218
<212> TYPE: PRT
<213> ORGANISM: Artificial
<220> FEATURE:
<223> OTHER INFORMATION: Synthetic

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 35
<211> LENGTH: 336
<212> TYPE: DNA
<213> ORGANISM: Artificial
<220> FEATURE:
<223> OTHER INFORMATION: Synthetic

<400> SEQUENCE: 35
gacattgtga tgacccaatc tccagactct ttggctgtgt ctctagggga gagggccacc    60
atcaactgca aggccagcca agtgttgat tttgatggtg atagttatct gaactggtac   120
caacagaaac caggacagcc acccaaactg ctcatctatg ctgcatccaa tctggaatct   180
ggggtgccag acaggtttag tggcagtggg tctgggacag acttcaccct caccatcagc   240
tccctgcagg ccgaggatgt ggcagtgtat tactgtcagc aaagtaatga ggatccgtgg   300
acgttcggtc agggcaccaa ggtggaaatc aaacga                             336

<210> SEQ ID NO 36
<211> LENGTH: 111
<212> TYPE: PRT
<213> ORGANISM: Artificial
<220> FEATURE:
<223> OTHER INFORMATION: Synthetic

<400> SEQUENCE: 36

Asp Ile Val Met Thr Gln Ser Pro Asp Ser Leu Ala Val Ser Leu Gly
1               5                   10                  15

```
Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys
            100                 105                 110

<210> SEQ ID NO 37
<211> LENGTH: 714
<212> TYPE: DNA
<213> ORGANISM: Artificial
<220> FEATURE:
<223> OTHER INFORMATION: Synthetic

<400> SEQUENCE: 37
atggagacag acacaatcct gctatgggtg ctgctgctct gggttccagg ctccactggt      60
gacattgtga tgacccaatc tccagactct ttggctgtgt ctctagggga gagggccacc     120
atcaactgca aggccagcca agtgttgat tttgatggtg atagttatct gaactggtac      180
caacagaaac aggacagcc acccaaactg ctcatctatg ctgcatccaa tctggaatct      240
ggggtgccag acaggtttag tggcagtggg tctgggacag acttcaccct caccatcagc     300
tccctgcagg ccgaggatgt ggcagtgtat tactgtcagc aaagtaatga ggatccgtgg     360
acgttcggtc agggcaccaa ggtggaaatc aaacgaactg tggcggcgcc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660 acccatcagg gcctgagctc gcccgtcaca aagagcttca caggggaga gtgt            714

<210> SEQ ID NO 38
<211> LENGTH: 238
<212> TYPE: PRT
<213> ORGANISM: Artificial
<220> FEATURE:
<223> OTHER INFORMATION: Synthetic

<400> SEQUENCE: 38

Met Glu Thr Asp Thr Ile Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Lys Ala Ser Gln Ser
        35                  40                  45

Val Asp Phe Asp Gly Asp Ser Tyr Leu Asn Trp Tyr Gln Gln Lys Pro
50                  55                  60

Gly Gln Pro Pro Lys Leu Leu Ile Tyr Ala Ala Ser Asn Leu Glu Ser
65                  70                  75                  80

Gly Val Pro Asp Arg Phe Ser Gly Ser Gly Ser Gly Thr Asp Phe Thr
                85                  90                  95
```

```
Leu Thr Ile Ser Ser Leu Gln Ala Glu Asp Val Ala Val Tyr Tyr Cys
            100                 105                 110

Gln Gln Ser Asn Glu Asp Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 39
<211> LENGTH: 218
<212> TYPE: PRT
<213> ORGANISM: Artificial
<220> FEATURE:
<223> OTHER INFORMATION: Synthetic

<400> SEQUENCE: 39

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 40
<211> LENGTH: 336
<212> TYPE: DNA
<213> ORGANISM: Artificial
<220> FEATURE:
<223> OTHER INFORMATION: Synthetic

<400> SEQUENCE: 40

```
gacattgtga tgacccaatc tccagactct ttggctgtgt ctctagggga gagggccacc        60
atcaactgca agtccagcca agtgttgat tttgatggtg atagttatct gaactggtac       120
caacagaaac caggacagcc acccaaactg ctcatctatg ctgcatccaa tctggaatct       180
ggggtgccag acaggtttag tggcagtggg tctgggacag acttcaccct caccatcagc       240
tccctgcagg ccgaggatgt ggcagtgtat tactgtcagc aaagtaatga ggatccgtgg       300
acgttcggtc agggcaccaa ggtggaaatc aaacga                                 336
```

<210> SEQ ID NO 41
<211> LENGTH: 111
<212> TYPE: PRT
<213> ORGANISM: Artificial
<220> FEATURE:
<223> OTHER INFORMATION: Synthetic

<400> SEQUENCE: 41

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys
            100                 105                 110
```

<210> SEQ ID NO 42
<211> LENGTH: 714
<212> TYPE: DNA
<213> ORGANISM: Artificial
<220> FEATURE:
<223> OTHER INFORMATION: Synthetic

<400> SEQUENCE: 42

```
atggagacag acacaatcct gctatgggtg ctgctgctct gggttccagg ctccactggt        60
gacattgtga tgacccaatc tccagactct ttggctgtgt ctctagggga gagggccacc       120
atcaactgca agtccagcca agtgttgat tttgatggtg atagttatct gaactggtac       180
caacagaaac caggacagcc acccaaactg ctcatctatg ctgcatccaa tctggaatct       240
ggggtgccag acaggtttag tggcagtggg tctgggacag acttcaccct caccatcagc       300
tccctgcagg ccgaggatgt ggcagtgtat tactgtcagc aaagtaatga ggatccgtgg       360
acgttcggtc agggcaccaa ggtggaaatc aaacgaactg tggcggcgcc atctgtcttc       420
atcttcccgc catctgatga gcagttgaaa tctggaactg cctctgttgt gtgcctgctg       480
aataacttct atcccagaga ggccaaagta cagtggaagg tggataacgc cctccaatcg       540
```

```
ggtaactccc aggagagtgt cacagagcag acagcaagg acagcaccta cagcctcagc      600
agcaccctga cgctgagcaa agcagactac gagaaacaca aagtctacgc ctgcgaagtc      660
acccatcagg gcctgagctc gcccgtcaca aagagcttca caggggaga gtgt             714
```

<210> SEQ ID NO 43
<211> LENGTH: 238
<212> TYPE: PRT
<213> ORGANISM: Artificial
<220> FEATURE:
<223> OTHER INFORMATION: Synthetic

<400> SEQUENCE: 43

```
Met Glu Thr Asp Thr Ile Leu Leu Trp Val Leu Leu Trp Val Pro
1               5                   10                  15

Gly Ser Thr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Val Asp Phe Asp Gly Asp Ser Tyr Leu Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
                100                 105                 110

Gln Gln Ser Asn Glu Asp Pro Trp Thr Phe Gly Gln Gly Thr Lys Val
            115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
    195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 44
<211> LENGTH: 218
<212> TYPE: PRT
<213> ORGANISM: Artificial
<220> FEATURE:
<223> OTHER INFORMATION: Synthetic

<400> SEQUENCE: 44

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Phe Asp
                20                  25                  30

Gly Asp Ser Tyr Leu Asn Trp Tyr Gln Gln Lys Pro Gly Gln Pro Pro
            35                  40                  45
```

Lys Leu Leu Ile Tyr Ala Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 45
<211> LENGTH: 117
<212> TYPE: PRT
<213> ORGANISM: Homo sapiens
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(66)
<223> OTHER INFORMATION: Xaa can be any naturally occurring amino acid
<220> FEATURE:
<221> NAME/KEY: misc_feature
<222> LOCATION: (96)..(108)
<223> OTHER INFORMATION: Xaa can be any naturally occurring amino acid

<400> SEQUENCE: 45

Gln Val Gln Leu Val Gln Ser Gly Ala Glu Val Lys Lys Pro Gly Ala
 1                5                  10                  15

Ser Val Lys Val Ser Cys Lys Ala Ser Gly Tyr Thr Phe Thr Xaa Xaa
                 20                  25                  30

Xaa Xaa Xaa Trp Val Arg Gln Ala Pro Gly Gln Gly Leu Glu Trp Met
            35                  40                  45

Gly Xaa Xaa Xaa Xaa Xaa Xaa Xaa Xaa Xaa Xaa Xaa Xaa Xaa Xaa Xaa
 50                  55                  60

Xaa Xaa Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Xaa
                 85                  90                  95

Xaa Xaa Xaa Xaa Xaa Xaa Xaa Xaa Xaa Xaa Xaa Xaa Gln Gly Thr Leu
            100                 105                 110

Val Thr Val Ser Ser
            115

<210> SEQ ID NO 46
<211> LENGTH: 111

-continued

```
<212> TYPE: PRT
<213> ORGANISM: Homo sapiens
<220> FEATURE:
<221> NAME/KEY: misc_feature
<222> LOCATION: (24)..(38)
<223> OTHER INFORMATION: Xaa can be any naturally occurring amino acid
<220> FEATURE:
<221> NAME/KEY: misc_feature
<222> LOCATION: (54)..(60)
<223> OTHER INFORMATION: Xaa can be any naturally occurring amino acid
<220> FEATURE:
<221> NAME/KEY: misc_feature
<222> LOCATION: (93)..(101)
<223> OTHER INFORMATION: Xaa can be any naturally occurring amino acid

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Xaa Xaa Xaa Xaa Xaa Xaa Xaa Xaa
            20                  25                  30

Xaa Xaa Xaa Xaa Xaa Xaa Trp Tyr Gln Gln Lys Pro Gly Gln Pro Pro
        35                  40                  45

Lys Leu Leu Ile Tyr Xaa Xaa Xaa Xaa Xaa Xaa Xaa Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Xaa Xaa Xaa Xaa
                85                  90                  95

Xaa Xaa Xaa Xaa Xaa Phe Gly Gln Gly Thr Lys Val Glu Ile Lys
            100                 105                 110
```